US008067584B2

(12) United States Patent
Starke et al.

(10) Patent No.: US 8,067,584 B2
(45) Date of Patent: *Nov. 29, 2011

(54) BENZOTHIAZEPINE DERIVATIVES

(75) Inventors: Ingemar Starke, Mölndal (SE);
Suzanne Alenfalk, Mölndal (SE); Mats Peter Nordberg, Mölndal (SE); Mikael Ulf Johan Dahlstrom, Mölndal (SE);
Stig Jonas Bostrom, Mölndal (SE);
Malin Anita Lemurell, Mölndal (SE);
Andreas Christer Wallberg, Mölndal (SE)

(73) Assignee: Albireo AB, Gothenburg (SE)

( * ) Notice: Subject to any disclaimer, the term of this patent is extended or adjusted under 35 U.S.C. 154(b) by 514 days.

This patent is subject to a terminal disclaimer.

(21) Appl. No.: 10/546,005

(22) PCT Filed: Feb. 23, 2004

(86) PCT No.: PCT/GB2004/000695
§ 371 (c)(1),
(2), (4) Date: Aug. 18, 2005

(87) PCT Pub. No.: WO2004/076430
PCT Pub. Date: Sep. 10, 2004

(65) Prior Publication Data
US 2006/0094884 A1 May 4, 2006

(30) Foreign Application Priority Data
Feb. 25, 2003 (GB) .................................. 0304194.4

(51) Int. Cl.
C07D 281/10 (2006.01)
A61K 31/554 (2006.01)
(52) U.S. Cl. .................................. 540/544; 514/211.09
(58) Field of Classification Search .................... 549/23;
540/544; 514/211.09
See application file for complete search history.

(56) References Cited

U.S. PATENT DOCUMENTS

| 5,811,388 | A | 9/1998 | Friend et al. | |
|---|---|---|---|---|
| 6,277,831 | B1 | 8/2001 | Frick et al. | |
| 6,346,527 | B1 | 2/2002 | Takanaka et al. | |
| 6,355,672 | B1 | 3/2002 | Yasuma et al. | |
| 6,387,924 | B2 | 5/2002 | Lee et al. | |
| 6,387,944 | B1 | 5/2002 | Frick et al. | |
| 6,906,058 | B2 | 6/2005 | Starke et al. | 514/211.1 |
| 6,943,189 | B2 | 9/2005 | Keller et al. | |
| 7,019,023 | B2 | 3/2006 | Frick et al. | |
| 7,125,864 | B2 | 10/2006 | Starke et al. | |
| 7,132,416 | B2 | 11/2006 | Starke et al. | |
| 7,132,557 | B2 | 11/2006 | Wilkes et al. | |
| 7,192,945 | B2 | 3/2007 | Starke et al. | |
| 7,192,946 | B2 * | 3/2007 | Starke et al. | 514/211.09 |
| 7,192,947 | B2 | 3/2007 | Starke et al. | |
| 7,226,943 | B2 | 6/2007 | Starke et al. | |
| 7,238,684 | B2 | 7/2007 | Starke et al. | |
| 7,514,421 | B2 | 4/2009 | Abrahamsson et al. | |
| 2002/0142054 | A1 | 10/2002 | Marlett et al. | 424/738 |
| 2005/0113362 | A1 | 5/2005 | Lindstedt et al. | |
| 2005/0124557 | A1 | 6/2005 | Lindqvist | |
| 2005/0171204 | A1 | 8/2005 | Lindstedt et al. | |
| 2005/0282822 | A1 | 12/2005 | Alstermark et al. | |
| 2006/0083790 | A1 | 4/2006 | Anderberg et al. | |

FOREIGN PATENT DOCUMENTS

| DE | 19825804 | 8/2000 |
|---|---|---|
| EP | 0372542 | 10/1992 |
| EP | 0 864 582 A | 9/1998 |
| GB | 2262888 | 7/1996 |
| WO | WO 93/16055 | 8/1993 |
| WO | WO 94/18183 | 8/1994 |
| WO | WO 94/18184 | 8/1994 |
| WO | WO 96/05188 A | 2/1996 |
| WO | WO 96/08484 A | 3/1996 |
| WO | WO 96/16051 | 5/1996 |
| WO | WO 97/33882 A | 9/1997 |
| WO | WO 98/38182 | 9/1998 |
| WO | WO 98/40375 | 9/1998 |
| WO | WO 99/01149 | 1/1999 |
| WO | WO 99/32478 | 7/1999 |
| WO | WO 99/35135 | 7/1999 |
| WO | WO 99/64409 | 12/1999 |
| WO | WO 99/64410 | 12/1999 |
| WO | WO 00/01687 A | 1/2000 |
| WO | WO 00/38725 | 7/2000 |
| WO | WO 00/38726 | 7/2000 |
| WO | WO 00/38727 | 7/2000 |
| WO | WO 00/38728 | 7/2000 |
| WO | WO 00/38729 | 7/2000 |
| WO | WO 00/47568 A | 8/2000 |
| WO | WO 00/61568 | 10/2000 |
| WO | WO 00/62810 | 10/2000 |
| WO | WO 01/60807 | 8/2001 |
| WO | WO 01/66533 | 9/2001 |
| WO | WO 01/68096 | 9/2001 |
| WO | WO 01/68637 | 9/2001 |
| WO | WO 02/08211 A | 1/2002 |
| WO | WO 02/32428 | 4/2002 |
| WO | WO 02/50051 | 6/2002 |
| WO | WO 02/053548 A1 | 7/2002 |
| WO | WO 03/020710 | 3/2003 |
| WO | WO 03/022286 | 3/2003 |
| WO | WO 03/022825 | 3/2003 |
| WO | WO 03/022825 A | 3/2003 |
| WO | WO 03/022830 | 3/2003 |
| WO | WO 03/051821 | 6/2003 |
| WO | WO 03/051822 | 6/2003 |
| WO | WO 03/061663 | 7/2003 |

(Continued)

OTHER PUBLICATIONS

Banker, G.S. et al, "Modern Pharmaceutics, 3ed.", Marcel Dekker, New York, 1996, pp. 451 and 596.*

(Continued)

Primary Examiner — David K O Dell
(74) Attorney, Agent, or Firm — Fish & Richardson P.C.

(57) ABSTRACT

Compounds of formula: (1) pharmaceutically acceptable salts, solvates, solvates of such salts and prodrugs thereof and their use as ileal bile acid transport (IBAT) inhibitors for the treatment of hyperlipidaemia are described. Processes for their manufacture and pharmaceutical compositions containing them are also described.

5 Claims, No Drawings

FOREIGN PATENT DOCUMENTS

| | | |
|---|---|---|
| WO | WO 03/091232 | 11/2003 |
| WO | WO 03/106482 | 12/2003 |
| WO | WO 2004/006899 | 1/2004 |
| WO | WO 2004/076430 | 9/2004 |
| WO | WO 2004/089350 | 10/2004 |

OTHER PUBLICATIONS

Wolff, Manfred E. "Burger's Medicinal Chemistry, 5ed, Part I", John Wiley & Sons, 1995, pp. 975-977.*

Tollefson et al. "A Novel Class of Apical Sodium Co-dependent Bile Acid Transporter Inhibitors: The 1,2-Benzothiazepines" Bioorganic & Medicinal Chemistry Letters 2003, 13, 3727-3730.*

Toshio Nagase et al. "Preparation of Benzothiazepine Derivatives With Activity of Bringing about High Blood GLP-1 Concentration", Database Caplus Chemical Abstracts Service, Columbus, Ohio.

M. C. Lewis et al. "Effects of 2164U90 on Ileal Bile Acid Absorption and Serum Cholesterol in Rats and Mice", Journal of Lipid Research, Bethesda, MD, vol. 36, No. 5, May 1995, pp. 1098-1105.

Govers et al. "Characterization of the adsorption of conjugated and unconjugated bile acids to insoluble, amorphous calcium phosphate" Journal of Lipid Research 35(5):741-748 (1994).

Higaki et al. "Inhibition of ileal Na+/bile acid cotransporter by S-8921 reduces serum cholesterol and prevents atherosclerosis in rabbits" Arteriosclerosis, Thrombosis, and Vascular Biology 18(8):1304-1311 (1998).

Ishibashi et al. "Hypercholesterolemia in low density lipoprotein receptor knockout mice and its reversal by adenovirus-mediated gene delivery" Journal of Clinical Investigation 92(2):883-893 (1993).

Plump et al. "Severe hypercholesterolemia and atherosclerosis in apolipoprotein E-deficient mice created by homologous recombination in ES cells" Cell (71):343-353 (1992).

Schiller "Review article: the therapy of constipation" Alimentary Pharmacology and Therapeutics 15(6):749-763 (2001).

Sprong et al. "Dietary Calcium Phosphate Promotes Listeria monocytogenes Colonization and Translocation in Rats Fed Diets Containing Corn Oil but Not Milk Fat I" J. Nutrition (US) 132(6):1269-1274 (2002).

Van Tilburg et al. "Na+-dependent bile acid transport in the ileum: the balance between diarrhea and constipation" Gastroenterology 98(1):25-32 (1989).

Welberg et al. "Calcium and the prevention of colon cancer" Scandinavian J. Gastroenterology Suppl. 188: 52-59 (1991).

* cited by examiner

BENZOTHIAZEPINE DERIVATIVES

This invention relates to benzothiazepine and benzothiepine derivatives, or pharmaceutically acceptable salts, solvates, solvates of such salts and prodrugs thereof. These benzothiazepines and benzothiepines possess ileal bile acid transport (IBAT) inhibitory activity and accordingly have value in the treatment of disease states associated with hyperlipidaemic conditions and they are useful in methods of treatment of a warm-blooded animal, such as man. The invention also relates to processes for the manufacture of said benzothiazepine and benzothiepine derivatives, to pharmaceutical compositions containing them and to their use in the manufacture of medicaments to inhibit IBAT in a warm-blooded animal, such as man.

It is well-known that hyperlipidaemic conditions associated with elevated concentrations of total cholesterol and low-density lipoprotein cholesterol are major risk factors for cardiovascular atherosclerotic disease (for instance "Coronary Heart Disease: Reducing the Risk; a Worldwide View" Assman G., Carmena R. Cullen P. et al; Circulation 1999, 100, 1930-1938 and "Diabetes and Cardiovascular Disease: A Statement for Healthcare Professionals from the American Heart Association" Grundy S, Benjamin I., Burke G., et al; Circulation, 1999, 100, 1134-46). Interfering with the circulation of bile acids within the lumen of the intestinal tracts is found to reduce the level of cholesterol. Previous established therapies to reduce the concentration of cholesterol involve, for instance, treatment with HMG-CoA reductase inhibitors, preferably statins such as simvastatin and fluvastatin, or treatment with bile acid binders, such as resins. Frequently used bile acid binders are for instance cholestyramine and cholestipol. One recently proposed therapy ("Bile Acids and Lipoprotein Metabolism: a Renaissance for Bile Acids in the Post Statin Era" Angelin B, Eriksson M, Rudling M; Current Opinion on Lipidology, 1999, 10, 269-74) involved the treatment with substances with an IBAT inhibitory effect.

Re-absorption of bile acid from the gastro-intestinal tract is a normal physiological process which mainly takes place in the ileum by the IBAT mechanism. Inhibitors of IBAT can be used in the treatment of hypercholesterolaemia (see for instance "Interaction of bile acids and cholesterol with non-systemic agents having hypocholesterolaemic properties", Biochemica et Biophysica Acta, 1210 (1994) 255-287). Thus, suitable compounds having such inhibitory IBAT activity are also useful in the treatment of hyperlipidaemic conditions. Substituted compounds possessing such IBAT inhibitory activity have been described, see for instance hypolipidaemic compounds described in WO 93/16055, WO 94/18183, WO 94/18184, WO 96/05188, WO 96/08484, WO 96/16051, WO 97/33882, WO 98/38182, WO 99/35135, WO 98/40375, WO 99/64409, WO 99/64410, WO 00/01687, WO 00/47568, WO 00/61568, DE 19825804, WO 00/38725, WO 00/38726, WO 00/38727, WO 00/38728, WO 00/38729, WO01/68096, WO 01/66533, WO 02/50051, WO 03/020710, WO 03/022825, WO 03/022830, WO 03/022286 and EP 0 864 582.

A further aspect of this invention relates to the use of the compounds of the invention in the treatment of dyslipidemic conditions and disorders such as hyperlipidaemia, hypertriglicerridemia, hyperbetalipoproteinemia (high LDL), hyperprebetalipoproteinemia (high VLDL), hyperchylomicronemia, hypolipoproteinemia, hypercholesterolemia, hyperlipoproteinemia and hypoalphalipoproteinemia (low HDL). In addition, these compounds are expected to be useful for the prevention and treatment of different clinical conditions such as atherosclerosis, arteriosclerosis, arrhythmia, hyper-thrombotic conditions, vascular dysfunction, endothelial dysfunction, heart failure, coronary heart diseases, cardiovascular diseases, myocardial infarction, angina pectoris, peripheral vascular diseases, inflammation of cardiovascular tissues such as heart, valves, vasculature, arteries and veins, aneurisms, stenosis, restenosis, vascular plaques, vascular fatty streaks, leukocytes, monocytes and/or macrophage infiltration, intimal thickening, medial thinning, infectious and surgical trauma and vascular thrombosis, stroke and transient ischaemic attacks.

The present invention is based on the discovery that certain benzothiazepine and benzothiepine compounds surprisingly inhibit IBAT. Such properties are expected to be of value in the treatment of disease states associated with hyperlipidaemic conditions.

Accordingly, the present invention provides a compound of formula (I):

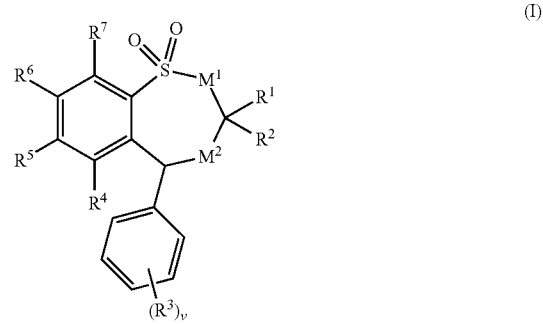

wherein
$M^1$ is —$CH_2$— or —$NR^{21}$—;
$M^2$ is —$CR^{22}R^{23}$— or —$NR^{24}$—; provided that if $M^1$ is —$NR^{21}$—, $M^2$ is —$CR^{22}R^{23}$—;
One of $R^1$ and $R^2$ are selected from hydrogen, $C_{1-6}$alkyl or $C_{2-6}$alkenyl and the other is selected from $C_{1-6}$alkyl or $C_{2-6}$alkenyl;
$R^3$ is selected from halo, nitro, cyano, hydroxy, amino, carboxy, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulphamoyl and N,N—($C_{1-6}$alkyl)$_2$sulphamoyl;
v is 0-5;
one of $R^5$ and $R^6$ is a group of formula (IA):

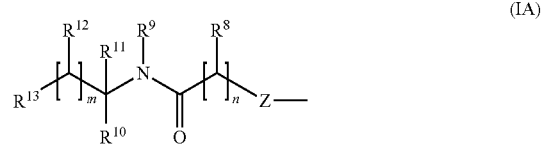

$R^4$ and $R^7$ and the other of $R^5$ and $R^6$ are independently selected from hydrogen, halo, nitro, cyano, hydroxy, amino, carboxy, carbamoyl, mercapto, sulphamoyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N—($C_{1-4}$alkyl)amino, N,N—($C_{1-4}$alkyl)$_2$amino, $C_{1-4}$alkanoylamino, N—($C_{1-4}$alkyl)carbamoyl, N,N—($C_{1-4}$alkyl)$_2$carbamoyl, $C_{1-4}$alkylS(O)$_a$ wherein a is 0 to 2, $C_{1-4}$alkoxycarbonyl, N—($C_{1-4}$alkyl)sulphamoyl and N,N—

$(C_{1-4}alkyl)_2$sulphamoyl; wherein $R^4$ and $R^7$ and the other of $R^5$ and $R^6$ may be optionally substituted on carbon by one or more $R^{25}$;

Z is —O—, —N($R^a$)—, —S(O)$_b$— or —CH($R^a$)—; wherein $R^a$ is hydrogen or $C_{1-6}$alkyl and b is 0-2;

$R^8$ is hydrogen, $C_{1-4}$alkyl, carbocyclyl or heterocyclyl; wherein $R^8$ may be optionally substituted on carbon by one or more substituents selected from $R^{26}$; and wherein if said heterocyclyl contains an —NH— group, that nitrogen may be optionally substituted by a group selected from $R^{27}$;

$R^9$ is hydrogen or $C_{1-4}$alkyl;

$R^{10}$ and $R^{11}$ are independently selected from hydrogen, $C_{1-4}$alkyl, carbocyclyl or heterocyclyl; or $R^{10}$ and $R^{11}$ together form $C_{2-6}$alkylene; wherein $R^{10}$ and $R^{11}$ or $R^{10}$ and $R^{11}$ together may be independently optionally substituted on carbon by one or more substituents selected from $R^{28}$; and wherein if said heterocyclyl contains an —NH— moiety, that nitrogen may be optionally substituted by one or more $R^{29}$;

$R^{12}$ is hydrogen, $C_{1-4}$alkyl, carbocyclyl or heterocyclyl; wherein $R^{12}$ may be optionally substituted on carbon by one or more substituents selected from $R^{30}$; and wherein if said heterocyclyl contains an —NH— moiety, that nitrogen may be optionally substituted by one or more $R^{31}$;

$R^{13}$ is hydrogen, halo, nitro, cyano, hydroxy, amino, carbamoyl, mercapto, sulphamoyl, hydroxyaminocarbonyl, $C_{1-10}$alkyl, $C_{2-10}$alkenyl, $C_{2-10}$alkynyl, $C_{1-10}$alkoxy, $C_{1-10}$alkoxycarbonyl, $C_{1-10}$alkanoyl, $C_{1-10}$alkanoyloxy, N—($C_{1-10}$alkyl)amino, N,N—($C_{1-10}$alkyl)$_2$amino, N,N,N—($C_{1-10}$alkyl)$_3$ammonio, $C_{1-10}$alkanoylamino, N—($C_{1-10}$alkyl)carbamoyl, N,N—($C_{1-10}$alkyl)$_2$carbamoyl, $C_{1-10}$alkylS(O)$_a$ wherein a is 0 to 2, N—($C_{1-10}$alkyl)sulphamoyl, N,N—($C_{1-10}$alkyl)$_2$sulphamoyl, N—($C_{1-10}$alkyl)sulphamoylamino, N,N—($C_{1-10}$allyl)$_2$sulphamoylamino, $C_{1-10}$alkoxycarbonylamino, carbocyclyl, carbocyclyl$C_{1-10}$alkyl, heterocyclic group, heterocyclyl$C_{1-10}$alkyl, carbocyclyl-($C_{1-10}$alkylene)$_e$-$R^{32}$—($C_{1-10}$alkylene)$_f$- or heterocyclyl-($C_{1-10}$alkylene)$_g$-$R^{33}$—($C_{1-10}$alkylene)$_h$-; wherein $R^{13}$ may be optionally substituted on carbon by one or more substituents selected from $R^{36}$; and wherein if said heterocyclyl contains an —NH— group, that nitrogen may be optionally substituted by a group selected from $R^{37}$; or $R^{13}$ is a group of formula (IB):

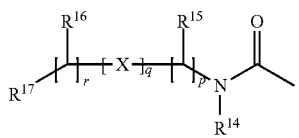

(IB)

wherein:

X is —N($R^{38}$)—, —N($R^{38}$)C(O)—, —O—, and —S(O)$_a$—; wherein a is 0-2 and $R^{38}$ is hydrogen or $C_{1-4}$alkyl;

$R^{14}$ is hydrogen or $C_{1-4}$alkyl;

$R^{15}$ and $R^{16}$ are independently selected from hydrogen, halo, nitro, cyano, hydroxy, amino, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoyl amino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulphamoyl, N,N—($C_{1-6}$alkyl)$_2$sulphamoyl, carbocyclyl or heterocyclic group; wherein $R^{15}$ and $R^{16}$ may be independently optionally substituted on carbon by one or more substituents selected from $R^{41}$; and wherein if said heterocyclyl contains an —NH— group, that nitrogen may be optionally substituted by a group selected from $R^{42}$;

$R^{17}$ is selected from hydrogen, halo, nitro, cyano, hydroxy, amino, carbamoyl, mercapto, sulphamoyl, hydroxyaminocarbonyl, $C_{1-10}$alkyl, $C_{2-10}$alkenyl, $C_{2-10}$alkynyl, $C_{1-10}$alkoxy, $C_{1-10}$alkanoyl, $C_{1-10}$alkanoyloxy, N—($C_{1-10}$alkyl)amino, N,N—($C_{1-10}$alkyl)$_2$amino, $C_{1-10}$alkanoylamino, N—($C_{1-10}$alkyl)carbamoyl, $C_{1-10}$alkoxycarbonyl, N,N—($C_{1-10}$alkyl)$_2$carbamoyl, $C_{1-10}$alkylS(O)$_a$ wherein a is 0 to 2, N—($C_{1-10}$alkyl)sulphamoyl, N,N—($C_{1-10}$alkyl)$_2$sulphamoyl, N—($C_{1-10}$alkyl)sulphamoylamino, N,N—($C_{1-10}$alkyl)$_2$sulphamoylamino, carbocyclyl, carbocyclyl$C_{1-10}$alkyl, heterocyclic group, heterocyclyl$C_{1-10}$alkyl, carbocyclyl-($C_{1-10}$alkylene)$_e$-$R^{43}$—($C_{1-10}$alkylene)$_f$- or heterocyclyl-($C_{1-10}$alkylene)$_g$-$R^{44}$—($C_{1-10}$alkylene)$_h$-; wherein $R^{17}$ may be optionally substituted on carbon by one or more substituents selected from $R^{47}$; and wherein if said heterocyclyl contains an —NH— group, that nitrogen may be optionally substituted by a group selected from $R^{48}$; or $R^{17}$ is a group of formula (IC):

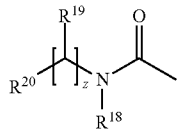

(IC)

wherein:

$R^{18}$ is selected from hydrogen or $C_{1-4}$alkyl;

$R^{19}$ is selected from hydrogen, halo, nitro, cyano, hydroxy, amino, carbamoyl, mercapto, sulphamoyl, $C_{1-6}$alkyl, $C_{2-6}$alkenyl, $C_{2-6}$alkynyl, $C_{1-6}$alkoxy, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulphamoyl, N,N—($C_{1-6}$alkyl)$_2$sulphamoyl, carbocyclyl or heterocyclic group; where $R^{19}$ may be independently optionally substituted on carbon by one or more substituents selected from $R^{51}$; and wherein if said heterocyclyl contains an —NH— group, that nitrogen may be optionally substituted by a group selected from $R^{52}$;

$R^{20}$ is selected from halo, nitro, cyano, hydroxy, amino, carbamoyl, mercapto, sulphamoyl, hydroxyaminocarbonyl, $C_{1-10}$alkyl, $C_{2-10}$alkenyl, $C_{2-10}$alkynyl, $C_{1-10}$alkoxy, $C_{1-10}$alkoxycarbonyl, $C_{1-10}$alkanoyl, $C_{1-10}$alkanoyloxy, N—($C_{1-10}$alkyl)amino, N,N—($C_{1-10}$alkyl)$_2$amino, N,N,N—($C_{1-10}$alkyl)$_3$ammonio, $C_{1-10}$alkanoylamino, N—($C_{1-10}$alkyl)carbamoyl, N,N—($C_{1-10}$alkyl)$_2$carbamoyl, $C_{1-10}$alkylS(O)$_a$ wherein a is 0 to 2, N—($C_{1-10}$alkyl)sulphamoyl, N,N—($C_{1-10}$alkyl)$_2$sulphamoyl, N—($C_{1-10}$alkyl)sulphamoylamino, N,N—($C_{1-10}$alkyl)$_2$sulphamoylamino, $C_{1-10}$alkoxycarbonylamino, carbocyclyl, carbocyclyl$C_{1-10}$allyl, heterocyclic group, heterocyclyl$C_{1-10}$alkyl, carbocyclyl-($C_{1-10}$alkylene)$_e$-$R^{53}$—($C_{1-10}$alkylene)$_f$- or heterocyclyl-($C_{1-10}$alkylene)$_g$-$R^{54}$—($C_{1-10}$alkylene)$_h$-; wherein $R^{20}$ may be independently optionally substituted on carbon by one or more $R^{57}$; and wherein if said heterocyclyl contains an —NH— group, that nitrogen may be optionally substituted by a group selected from $R^{58}$;

p is 1-3; wherein the values of $R^{15}$ may be the same or different;

q is 0-1;

r is 0-3; wherein the values of $R^{16}$ may be the same or different;

m is 0-2; wherein the values of $R^{12}$ may be the same or different;

n is 1-2; wherein the values of $R^{8}$ may be the same or different;

z is 0-3; wherein the values of $R^{19}$ may be the same or different;

$R^{21}$ is selected from hydrogen or $C_{1-6}$alkyl;

$R^{22}$ and $R^{23}$ are independently selected from hydrogen, hydroxy, amino, mercapto, $C_{1-6}$alkyl, $C_{1-6}$alkoxy, N—($C_{1-6}$alkyl)amino, N,N—($C_{1-6}$alkyl)$_2$amino, $C_{1-6}$alkylS(O)$_a$ wherein a is 0 to 2;

$R^{24}$ is selected from hydrogen, hydroxy, $C_{1-6}$alkyl, $C_{1-4}$alkoxy and $C_{1-6}$alkanoyloxy;

$R^{25}$ is selected from halo, nitro, cyano, hydroxy, amino, carboxy, carbamoyl, mercapto, sulphamoyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N—($C_{1-4}$alkyl)amino, N,N—($C_{1-4}$alkyl)$_2$amino, $C_{1-4}$alkanoylamino, N—($C_{1-4}$alkyl)carbamoyl, N,N—($C_{1-4}$alkyl)$_2$carbamoyl, $C_{1-4}$alkylS(O)$_a$ wherein a is 0 to 2, $C_{1-4}$alkoxycarbonyl, N—($C_{1-4}$alkyl)sulphamoyl and N,N—($C_{1-4}$alkyl)$_2$sulphamoyl; wherein $R^{25}$ may be independently optionally substituted on carbon by one or more $R^{67}$;

$R^{26}$, $R^{28}$, $R^{30}$, $R^{36}$, $R^{41}$, $R^{47}$, $R^{51}$ and $R^{57}$ are independently selected from halo, nitro, cyano, hydroxy, amino, carbamoyl, mercapto, sulphamoyl, hydroxyaminocarbonyl, $C_{1-10}$alkyl, $C_{2-10}$alkenyl, $C_{2-10}$alkynyl, $C_{1-10}$alkoxy, $C_{1-10}$alkanoyl, $C_{1-10}$alkanoyloxy, $C_{1-10}$alkoxycarbonyl, N—($C_{1-10}$alkyl)amino, N,N—($C_{1-10}$alkyl)$_2$amino, N,N,N—($C_{1-10}$alkyl)$_3$ammonio, $C_{1-10}$alkanoylamino, N—($C_{1-10}$alkyl)carbamoyl, N,N—($C_{1-10}$alkyl)$_2$carbamoyl, $C_{1-10}$alkylS(O)$_a$ wherein a is 0 to 2, N—($C_{1-10}$alkyl)sulphamoyl, N,N—($C_{1-10}$alkyl)$_2$sulphamoyl, N—($C_{1-10}$alkyl)sulphamoylamino, N,N—($C_{1-10}$alkyl)$_2$sulphamoylamino, $C_{1-10}$alkoxycarbonylamino, carbocyclyl, carbocyclyl$C_{1-10}$alkyl, heterocyclic group, heterocyclyl$C_{1-10}$alkyl, carbocyclyl-($C_{1-10}$alkylene)$_e$-$R^{59}$—($C_{1-10}$alkylene)$_f$- or heterocyclyl-($C_{1-10}$alkylene)$_g$-$R^{60}$—($C_{1-10}$alkylene)$_h$-; wherein $R^{26}$, $R^{28}$, $R^{30}$, $R^{36}$, $R^{41}$, $R^{47}$, $R^{51}$ and $R^{57}$ may be independently optionally substituted on carbon by one or more $R^{63}$; and wherein if said heterocyclyl contains an —NH— group, that nitrogen may be optionally substituted by a group selected from $R^{64}$;

$R^{27}$, $R^{29}$, $R^{31}$, $R^{37}$, $R^{42}$, $R^{48}$, $R^{52}$, $R^{58}$ and $R^{64}$ are independently selected from $C_{1-6}$alkyl, $C_{1-6}$alkanoyl, $C_{1-6}$alkylsulphonyl, sulphamoyl, N—($C_{1-6}$alkyl)sulphamoyl, N,N—($C_{1-6}$alkyl)$_2$sulphamoyl, $C_{1-6}$alkoxycarbonyl, carbamoyl, N—($C_{1-6}$alkyl)carbamoyl, N,N—($C_{1-6}$alkyl)$_2$carbamoyl, benzyl, phenethyl, benzoyl, phenylsulphonyl and phenyl;

$R^{32}$, $R^{33}$, $R^{43}$, $R^{44}$, $R^{53}$, $R^{54}$, $R^{59}$ and $R^{60}$ are independently selected from —O—, —NR$^{65}$—, —S(O)$_x$—, —NR$^{65}$C(O)NR$^{66}$—, —NR$^{65}$C(S)NR$^{66}$—, —OC(O)N=C—, —NR$^{65}$C(O)— or —C(O)NR$^{65}$—; wherein $R^{65}$ and $R^{66}$ are independently selected from hydrogen or $C_{1-6}$alkyl, and x is 0-2;

$R^{63}$ and $R^{67}$ are independently selected from halo, hydroxy, cyano, carbamoyl, ureido, amino, nitro, carbamoyl, mercapto, sulphamoyl, trifluoromethyl, trifluoromethoxy, methyl, ethyl, methoxy, ethoxy, vinyl, allyl, ethynyl, methoxycarbonyl, formyl, acetyl, formamido, acetylamino, acetoxy, methylamino, dimethylamino, N-methylcarbamoyl, N,N-dimethylcarbamoyl, methylthio, methylsulphinyl, mesyl, N-methylsulphamoyl and N,N-dimethylsulphamoyl; and e, f, g and h are independently selected from 0-2;

or a pharmaceutically acceptable salt, solvate, solvate of such a salt or a prodrug thereof.

In this specification the term "allyl" includes both straight and branched chain alkyl groups but references to individual alkyl groups such as "propyl" are specific for the straight chain version only. For example, "$C_{1-10}$alkyl" and "$C_{1-6}$alkyl" includes $C_{1-4}$alkyl, $C_{1-3}$alkyl, propyl, isopropyl and t-butyl. However, references to individual alkyl groups such as 'propyl' are specific for the straight chained version only and references to individual branched, chain alkyl groups such as 'isopropyl' are specific for the branched chain version only. A similar convention applies to other radicals, for example "phenyl$C_{1-6}$alkyl" would include phenyl$C_{1-6}$alkyl, benzyl, 1-phenylethyl and 2-phenylethyl. The term "halo" refers to fluoro, chloro, bromo and iodo.

Where optional substituents are chosen from "one or more" groups it is to be understood that this definition includes all substituents being chosen from one of the specified groups or the substituents being chosen from two or more of the specified groups.

A "heterocyclyl" is a saturated, partially saturated or unsaturated, mono or bicyclic ring containing 3-12 atoms of which at least one atom is chosen from nitrogen, sulphur or oxygen, which may, unless otherwise specified, be carbon or nitrogen linked, wherein a —CH$_2$— group can optionally be replaced by a —C(O)— or a ring sulphur atom may be optionally oxidised to form the S-oxides. Preferably a "heterocyclyl" is a saturated, partially saturated or unsaturated, mono or bicyclic ring containing 5 or 6 atoms of which at least one atom is chosen from nitrogen, sulphur or oxygen, which may, unless otherwise specified, be carbon or nitrogen linked, wherein a —CH$_2$— group can optionally be replaced by a —C(O)— or a ring sulphur atom may be optionally oxidised to form S-oxide(s). Examples and suitable values of the term "heterocyclyl" are thiazolidinyl, pyrrolidinyl, pyrrolinyl, 2-pyrrolidonyl, 2,5-dioxopyrrolidinyl, 2-benzoxazolinonyl, 1,1-dioxotetrahydrothienyl, 2,4-dioxoimidazolidinyl, 2-oxo-1,3,4-(4-triazolinyl), 2-oxazolidinonyl, 5,6-dihydrouracilyl, 1,3-benzodioxolyl, 1,2,4-oxadiazolyl, 2-azabicyclo[2.2.1]heptyl, 4-thiazolidonyl, morpholino, 2-oxotetrahydrofuranyl, tetrahydrofuranyl, 2,3-dihydrobenzofuranyl, benzothienyl, tetrahydropyranyl, piperidyl, 1-oxo-1,3-dihydroisoindolyl, piperazinyl, thiomorpholino, 1,1-dioxothiomorpholino, tetrahydropyranyl, 1,3-dioxolanyl, homopiperazinyl, thienyl, isoxazolyl, imidazolyl, pyrrolyl, thiadiazolyl, isothiazolyl, 1,2,4-triazolyl, 1,3,4-triazolyl, pyranyl, indolyl, pyrimidyl, thiazolyl, pyrazinyl, pyridazinyl, pyridyl, 4-pyridonyl, quinolyl and 1-isoquinolonyl.

A "heterocyclic group" is a saturated, partially saturated or unsaturated, mono or bicyclic ring containing 3-12 atoms of which at least one atom is chosen from nitrogen, sulphur or oxygen, which may, unless otherwise specified, be carbon or nitrogen linked, wherein a —CH$_2$— group can optionally be replaced by a —C(O)— or a ring sulphur atom may be optionally oxidised to form the S-oxides. A "heterocyclic group" is not tetrazolyl. Preferably a "heterocyclic group" is a saturated, partially saturated or unsaturated, monocyclic ring containing 5 or 6 atoms or a bicyclic ring containing 9 or 10 atoms of which at least one atom is chosen from nitrogen, sulphur or oxygen, which may, unless otherwise specified, be carbon or nitrogen linked, wherein a —CH$_2$— group can optionally be replaced by a —C(O)— or a ring sulphur atom may be optionally oxidised to form S-oxide(s). Examples and suitable values of the term "heterocyclic group" are thiazolidinyl, pyrrolidinyl, pyrrolinyl, 2-pyrrolidonyl, 2,5-dioxopyrrolidinyl, 2-benzoxazolinonyl, 1,1-dioxotetrahydrothienyl, 2,4-dioxoimidazolidinyl, 2-oxo-1,3,4-(4triazolinyl), 2-oxazolidinonyl, 5,6-dihydrouracilyl, 1,3-benzodioxolyl, 1,2,4-oxadiazolyl, 2-azabicyclo[2.2.1]heptyl, 4-thiazolidonyl, morpholino, 2-oxotetrahydrofuranyl, tetrahydrofuranyl, 2,3-dihydrobenzofuranyl, benzothienyl, tetrahydropyranyl, piperidyl, 1-oxo-1,3-dihydroisoindolyl, piperazinyl, thiomorpholino, 1,1-dioxothiomorpholino, tetrahydropyranyl, 1,3-dioxolanyl, homopiperazinyl, thienyl, isoxazolyl, imidazolyl, pyrrolyl, thiadiazolyl, isothiazolyl, 1,2,4-triazolyl, 1,3,4-triazolyl, pyranyl, indolyl, pyrimidyl, thiazolyl, pyrazinyl, pyridazinyl, pyridyl, 4-pyridonyl, quinolyl and 1-isoquinolonyl.

A "carbocyclyl" is a saturated, partially saturated or unsaturated, mono or bicyclic carbon ring that contains 3-12 atoms; wherein a —$CH_2$— group can optionally be replaced by a —C(O)—. Preferably "carbocyclyl" is a monocyclic ring containing 5 or 6 atoms or a bicyclic ring containing 9 or 10 atoms. Suitable values for "carbocyclyl" include cyclopropyl, cyclobutyl, 1-oxocyclopentyl, cyclopentyl, cyclopentenyl, cyclohexyl, cyclohexenyl, phenyl, naphthyl, tetralinyl, indanyl or 1-oxoindanyl. Particularly "carbocyclyl" is cyclopropyl, cyclobutyl, 1-oxocyclopentyl, cyclopentyl, cyclopentenyl, cyclohexyl, cyciohexenyl, phenyl or 1-oxoindanyl.

An example of "$C_{1-10}$alkanoyloxy" and "$C_{1-6}$alkanoyloxy" is acetoxy. Examples of "$C_{1-10}$alkoxycarbonyl" and "$C_{1-6}$alkoxycarbonyl" include methoxycarbonyl, ethoxycarbonyl, n- and t-butoxycarbonyl. Examples of "$C_{1-10}$alkoxy" and "$C_{1-6}$alkoxy" include methoxy, ethoxy and propoxy. Examples of "$C_{1-10}$alkanoylamino" and "$C_{1-6}$alkanoylamino" include formamido, acetamido and propionylamino. Examples of "$C_{1-6}$alkanoyl-N—($C_{1-6}$alkyl)amino" include acetyl-N-methylamino and propionyl-N-ethyl-amino. Examples of "$C_{1-10}$alkylS(O)$_a$ wherein a is 0 to 2" and "$C_{1-6}$alkylS(O)$_a$ wherein a is 0 to 2" include methylthio, ethylthio, methylsulphinyl, ethylsulphinyl, mesyl and ethylsulphonyl. Examples of "$C_{1-10}$alkanoyl" and "$C_{1-6}$alkanoyl" include $C_{1-3}$alkanoyl, propionyl and acetyl. Examples of "N—($C_{1-10}$alkyl)amino" and "N—($C_{1-6}$alkyl)amino" include methylamino and ethylamino. Examples of "N,N—($C_{1-10}$alkyl)$_2$amino" and "N,N—($C_{1-6}$alkyl)$_2$amino" include di-N-methylamino, di-(N-ethyl)amino and N-ethyl-N-methylamino. Examples of "$C_{2-10}$alkenyl" and "$C_{2-6}$alkenyl" are vinyl, allyl and 1-propenyl. Examples of "$C_{2-10}$alkynyl" and "$C_{2-6}$alkynyl" are ethynyl, 1-propynyl and 2-propynyl. Examples of "$C_{2-6}$alkylene" are ethylene, propylene and butylene. Examples of "$C_{2-6}$alkenyloxy" are vinyloxy, allyloxy and 1-propenyloxy. Examples of "N—($C_{1-10}$alkyl)sulphamoyl" and "N—($C_{1-6}$alkyl)sulphamoyl" are N—($C_{1-3}$alkyl)sulphamoyl, N-(methyl)sulphamoyl and N-(ethyl)sulphamoyl. Examples of "N—($C_{1-10}$alkyl)$_2$sulphamoyl" and "N—($C_{1-6}$alkyl)$_2$sulphamoyl" are N,N-(dimethyl)sulphamoyl and N-(methyl)-N-(ethyl)sulphamoyl. Examples of "N—($C_{1-10}$alkyl)carbamoyl" and "N—($C_{1-6}$alkyl)carbamoyl" are methylaminocarbonyl and ethylaminocarbonyl. Examples of "N,N—($C_{1-10}$alkyl)$_2$carbamoyl" and "N,N—($C_{1-6}$alkyl)$_2$carbamoyl" are dimethylaminocarbonyl and methylethylaminocarbonyl. Examples of "N—($C_{1-10}$alkyl)carbamoyl" and "N—($C_{1-6}$alkyl)carbamoyloxy" are methylaminocarbonyloxy and ethylaminocarbonyloxy. Examples of "N,N—($C_{1-10}$alkyl)$_2$carbamoyl" and "N,N—($C_{1-6}$alkyl)$_2$carbamoyloxy" are dimethylaminocarbonyloxy and methylethylaminocarbonyloxy. Examples of "$C_{1-6}$alkylsulphonyl" are mesyl and ethylsulphonyl. Examples of "$C_{1-10}$alkylsulphonylamino" and "$C_{1-6}$alkylsulphonylamino" are mesylamino and ethylsulphonylamino. Examples of "$C_{1-6}$alkylsulphonyl-N—($C_{1-6}$alkyl)amino" are mesyl-N-methylamino and ethylsulphonyl-N-propylamino. Examples of "N'—($C_{1-6}$alkyl)ureido" are N'-methylureido and N'-i-propylureido. Examples of "N—($C_{1-6}$alkyl)ureido" are N-methylureido and N-i-propylureido. Examples of "N',N'—($C_{1-6}$alkyl)$_2$ureido" are N',N'-dimethylureido and N'-methyl-N'-ethylureido. Examples of "N'—($C_{1-6}$alkyl)-N—($C_{1-6}$alkyl)ureido" are N',N-dimethylureido and N'-methyl-N-ethylureido. Examples of "N',N'—($C_{1-6}$alkyl)$_2$-N—($C_{1-6}$alkyl)ureido" are N',N'-dimethyl-N-methylureido and N'-methyl-N'-ethyl-N-t-butylureido. Examples of "N,N,N—($C_{1-10}$alkyl)$_3$ammonio" are trimethylamino and methyldiethylamino. Examples of "$C_{1-10}$alkoxycarbonylamino" and "$C_{1-6}$alkoxycarbonylamino" are methoxycarbonylamino and t-butoxycarbonylamino. Examples of "N—($C_{1-10}$alkyl)sulphamoylamino" are N-methylsulphamoylamino and N-ethylsulphamoylamino. Examples of "N,N—($C_{1-10}$alkyl)$_2$sulphamoylamino" are N,N-dimethylsulphamoylamino and N-methyl-N-ethylsulphamoylamino. Examples of "carbocyclyl$C_{1-10}$alkyl" include benzyl and phenethyl. Examples of "heterocyclyl$C_{1-10}$alkyl" include 2-morphoinopropyl and pyridylmethyl. Examples of "phenyl$C_{1-6}$alkoxy" include 2-phenylethoxy and 2-phenylpropoxy.

A suitable pharmaceutically acceptable salt of a compound of the invention is, for example, an acid-addition salt of a compound of the invention which is sufficiently basic, for example, an acid-addition salt with, for example, an inorganic or organic acid, for example hydrochloric, hydrobromic, sulphuric, phosphoric, trifluoroacetic, citric, acetate or maleic acid. In addition a suitable pharmaceutically acceptable salt of a compound of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl) amine.

The compounds of the formula (I) may be administered in the form of a pro-drug which is broken down in the human or animal body to give a compound of the formula (I). examples of pro-drugs include in vivo hydrolysable esters and in vivo hydrolysable amides of a compound of the formula (I).

An in vivo hydrolysable ester of a compound of the formula (I) containing carboxy or hydroxy group is, for example, a pharmaceutically acceptable ester which is hydrolysed in the human or animal body to produce the parent acid or alcohol. Suitable pharmaceutically acceptable esters for carboxy include $C_{1-6}$alkoxymethyl esters for example methoxymethyl, $C_{1-6}$alkanoyloxymethyl esters for example pivaloyloxymethyl, phthalidyl esters, $C_{3-8}$cycloalkoxycarbonyloxy$C_{1-6}$alkyl esters for example 1-cyclohexylcarbonyloxyethyl; 1,3-dioxolen-2-onylmethyl esters for example 5-methyl-1,3-dioxolen-2-onylmethyl; and $C_{1-6}$alkoxycarbonyloxyethyl esters for example 1-methoxycarbonyloxyethyl and may be formed at any carboxy group in the compounds of this invention.

An in vivo hydrolysable ester of a compound of the formula (I) containing a hydroxy group includes inorganic esters such as phosphate esters and α-acyloxyalkyl ethers and related compounds which as a result of the in vivo hydrolysis of the ester breakdown to give the parent hydroxy group. Examples of α-acyloxyalkyl ethers include acetoxymethoxy and 2,2-dimethylpropionyloxy-methoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl. Examples of substituents on benzoyl include morpholino and piperazino linked from a ring nitrogen atom via a methylene group to the 3- or 4-position of the benzoyl ring.

A suitable value for an in vivo hydrolysable amide of a compound of the formula (I) containing a carboxy group is, for example, a N—$C_{1-6}$alkyl or N,N-di-$C_{1-6}$alkyl amide such as N-methyl, N-ethyl, N-propyl, N,N-dimethyl, N-ethyl-N-methyl or N,N-diethyl amide.

Some compounds of the formula (I) may have chiral centres and/or geometric isomeric centres (E- and Z-isomers), and it is to be understood that the invention encompasses all such optical, diastereoisomers and geometric isomers that possess IBAT inhibitory activity.

The invention relates to any and all tautomeric forms of the compounds of the formula (I) that possess IBAT inhibitory activity.

It is also to be understood that certain compounds of the formula (I) can exist in solvated as well as unsolvated forms such as, for example, hydrated forms. It is to be understood that the invention encompasses all such solvated forms which possess IBAT inhibitory activity.

Particular values are as follows. Such values may be used where appropriate with any of the definitions, claims or embodiments defined hereinbefore or hereinafter.

$M^1$ is —$CH_2$—.
$M^1$ is —$NR^{21}$—.
$M^2$ is —$CR^{22}R^{23}$—.
$M^2$ is —$NR^{24}$—.
$M^1$ is —$CH_2$— and M is —$CR^{22}R^{23}$—.
$M^1$ is —$CH_2$— and $M^2$ is —$NR^{24}$—.
$M^1$ is —$NR^{21}$— and $M^2$ is —$CR^{22}R^{23}$—.
$R^{21}$ is hydrogen.
$R^{21}$ is $C_{1-6}$alkyl.
$R^{22}$ and $R^{23}$ are independently selected from hydrogen and hydroxy.
One of $R^{22}$ and $R^{23}$ is hydrogen and the other is hydroxy.
$R^{24}$ is hydrogen.
$R^1$ and $R^2$ are $C_{1-4}$alkyl.
$R^1$ and $R^2$ are both butyl.
One of $R^1$ and $R^2$ is ethyl and the other is butyl.
v is 0.
$R^3$ is $C_{1-4}$alkyl.
$R^5$ is a group of formula (IA).
$R^6$ is a group of formula (IA).
$R^4$ and $R^7$ are hydrogen.
$R^5$ is methylthio and $R^6$ is a group of formula (IA).
The $R^5$ or $R^6$ not selected from a group of formula (IA) is hydrogen, halo, $C_{1-4}$alkyl or $C_{1-4}$alkylS(O)$_a$ wherein a is 0.
The $R^5$ or $R^6$ not selected from a group of formula (IA) is hydrogen, bromo, methyl or methylthio.
The $R^5$ or $R^6$ not selected from a group of formula (IA) is hydrogen or methylthio.
The $R^5$ or $R^6$ not selected from a group of formula (IA) is hydrogen.
The $R^5$ or $R^6$ not selected from a group of formula (IA) is methylthio.

The group of formula (IA) is selected from:
N—{(R)-α-[N'-(2-hydroxyethyl)carbamoyl]benzyl}carbamoylmethoxy;
N—{(R)-α-[N'-(2-trimethylaminoethyl)carbamoyl]benzyl}carbamoylmethoxy;
N—{(R)-α-[N'-(2-aminoethyl)carbamoyl]benzyl}carbamoylmethoxy;
N—{(R)-α-[N'-(carbamoylmethyl)carbamoyl]benzyl}carbamoylmethoxy;
N—{(R)-α-[N'-((S)-1-carbamoyl-2-hydroxyethyl)carbamoyl]benzyl}carbamoylmethoxy;
N—((R)-α-carbamoylbenzyl)carbamoylmethoxy;
N—{(R)-α-[N'-(1,1-di-hydroxymethyl-2-hydroxyethyl)carbamoyl]benzyl}carbamoylmethoxy;
N—{(R)-α-[N'-(hydroxycarbamoylmethyl)carbamoyl]benzyl}carbamoylmethoxy;
N—((R)-α-{N'-[N-(2,2,2-trifluoroethyl)carbamoylmethyl]carbamoyl}benzyl)carbamoylmethoxy;
N—((R)-α-{N'-[N-(2-(S)-3-(R)-4-(R)-5-(R)-2,3,4,5,6-pentahydroxyhexyl)carbamoylmethyl]carbamoyl}benzyl)carbamoylmethoxy;
N—((R)-α-{N'-[N-(2-fluoroethyl)carbamoylmethyl]carbamoyl}benzyl)carbamoylmethoxy;
N—((R)-α-{N'-[N-(ethyl)carbamoylmethyl]carbamoyl}benzyl)carbamoylmethoxy;
N—((R)-α-{N'-[N-(4-hydroxy-3-methoxybenzyl)carbamoylmethyl]carbamoyl}benzyl)carbamoylmethoxy;
N—((R)-α-{N'-[N-(2-methoxyethyl)carbamoylmethyl]carbamoyl}benzyl)carbamoylmethoxy;
N—((R)-α-{N'-[N-(4-sulphamoylphenethyl)carbamoylmethyl]carbamoyl}benzyl)carbamoylmethoxy;
N—((R)-α-{N—[N-(2-N,N-dimethylaminosulphamoylethyl)carbamoylmethyl]carbamoyl}benzyl)carbamoylmethoxy;
N—[(R)-α-(N'-(N-[2-(N'-pyrimidin-2-ylureido)ethyl]carbamoylmethyl}carbamoyl)benzyl]carbamoylmethoxy;
N—{(R)-α-[N'-(2-(S)-3-(R)-4-(R)-5-(R)-2,3,4,5,6-pentahydroxyhexyl)carbamoyl]benzyl}carbamoylmethoxy;
N—{(R)-α-[N'-(3-morpholinopropyl)carbamoyl]benzyl}carbamoylmethoxy;
N—{(R)-α-[N'-(2-imidazol-4-ylethyl)carbamoyl]benzyl}carbamoylmethoxy;
N—{(R)-α-[N'-(2-N,N-dimethylaminosulphamoylethyl)carbamoyl]benzyl}carbamoylmethoxy;
N—((R)-α-{N'-[2-(2-hydroxyphenoxy)ethyl]carbamoyl}benzyl)carbamoylmethoxy;
N—{(R)-α-[N'-(3-hydroxy-1,5-benzodioxepin-3-ylmethyl)carbamoyl]benzyl}carbamoylmethoxy;
N—{(R)-α-[N'-(3-t-butoxycarbonylaminobenzyl)carbamoyl]benzyl}carbamoylmethoxy;
N—((R)-α-{N'-[3-(benxyloxycarbonylimino-1-aminomethyl)benzyl]carbamoyl}benzyl)carbamoylmethoxy;
N—((R)-α-{N'-[2-(3,4-dihydroxyphenyl)-2-methoxyethyl]carbamoyl}benzyl)carbamoylmethoxy;
N—{(R)-α-[N'-(2,3-dihydroxypropyl)carbamoyl]benzyl}carbamoylmethoxy;
N—((R)-α-{N'-[2-(5-methoxyindol-3-yl)ethyl]carbamoyl}benzyl)carbamoylmethoxy;
N—((R)-α-{N'-[2-(2,5-dioxothiazolidin-1-yl)ethyl]carbamoyl}benzyl)carbamoylmethoxy;
N—((R)-α-{N'-[3-(4-methylpiperazin-1-yl)propyl]carbamoyl}benzyl)carbamoylmethoxy;
N—{(R)-α-[N'-(4-sulphamoylphenethyl)carbamoyl]benzyl}carbamoylmethoxy;
N—{(R)-α-[N'-(5,6-dimethoxy-2,3-dihydrobenzofuran-2-ylmethyl)carbamoyl]benzyl}carbamoylmethoxy;
N—{(R)-α-[N'-(1-t-butoxycarbonylpiperidin-4-ylmethyl)carbamoyl]benzyl}carbamoylmethoxy;
N—{(R)-α-[N'-(4-nitroanilnocarbonylmethyl)carbamoyl]benzyl}carbamoylmethoxy;
N—((R)-α-{N'-[2-(N'-pyrimidin-2-ylureido)ethyl]carbamoyl}benzyl)carbamoylmethoxy;
N—((R)-α-{N'-[2-(N'-pyridin-2-ylureido)ethyl]carbamoyl}benzyl)carbamoylmethoxy;
N—((R)-α-{N'-[2-(4-carbamoylphenoxy)ethyl]carbamoyl}benzyl)carbamoylmethoxy;
N—((R)-α-{N'-[2-(2-oxoimidazolidin-1-yl)ethyl]carbamoyl}benzyl)carbamoylmethoxy; and
N—{(R)-α-[N'-(3-aminobenzyl)carbamoyl]benzyl}carbamoylmethoxy.

The group of formula (IA) is selected from:
N—{α-[N'-(2-(S)-3-R)-4-(R)-5-(R)-2,3,4,5,6-pentahdroxyhexyl)carbamoyl]-2-fluorobenzyl}carbamoylmethylthio;
N—{1-[N'-(2-(S)-3-(R)-4-(R)-5-(R)-2,3,4,5,6-pentahydroxyhexyl)carbamoyl]-1-(cyclohexyl)methyl}carbamoylmethylthio;
N—{(R)-α-[N'-(2-(S)-3-(R)-4-(R)-5-(R)-2,3,4,5,6-pentahydroxyhexyl)carbamoyl]benzyl}carbamoylmethoxy;
N—{(R)-α-[N'-(2-(S)-3-(R)-4-(R)-5-(R)-2,3,4,5,6-pentahydroxyhexyl)carbamoyl]benzyl}carbamoylmethoxy.

Z is —O— or —S(O)$_b$—; wherein b is 0.

R$^8$ is hydrogen.

R$^9$ is hydrogen.

R$^{10}$ and R$^{11}$ are independently selected from hydrogen or carbocyclyl; wherein R$^{10}$ and R$^{11}$ may be independently optionally substituted on carbon by one or more substituents selected from R$^{28}$.

R$^{10}$ and R$^{11}$ are independently selected from hydrogen, cyclohexyl or phenyl; wherein R$^{10}$ and R$^{11}$ may be independently optionally substituted on carbon by one or more substituents selected from halo.

R$^{10}$ and R$^{11}$ are independently selected from hydrogen, cyclohexyl or 2-fluorophenyl.

R$^{13}$ is a group of formula (IB).

R$^{14}$ is hydrogen.

R$^{15}$ is hydrogen.

R$^{17}$ is C$_{1-10}$alkyl; wherein R$^{17}$ may be optionally substituted on carbon by one or more substituents selected from R$^{47}$ or R$^{17}$ is a group of formula (IC) (as depicted above).

R$^{17}$ is C$_{1-10}$alkyl; wherein R$^{17}$ may be optionally substituted on carbon by one or more substituents selected from R$^{47}$ or R$^{17}$ is a group of formula (IC) (as depicted above).

R$^{17}$ is C$_{1-6}$alkyl; wherein R$^{17}$ may be optionally substituted on carbon by one or more hydroxy or R$^{17}$ is a group of formula (IC) (as depicted above).

R$^{17}$ is pentyl substituted by 5 hydroxy or R$^{17}$ is a group of formula (IC) (as depicted above).

R$^{18}$ is selected from hydrogen.

R$^{19}$ is selected from hydrogen.

R$^{20}$ is C$_{1-10}$alkyl; wherein R$^{20}$ may be independently optionally substituted on carbon by one or more R$^{57}$.

R$^{20}$ is C$_{1-10}$alkyl; wherein R$^{20}$ may be independently optionally substituted on carbon by one or more hydroxy.

R$^{20}$ is pentyl substituted by 5 hydroxy.

p is 1.

q is 0.

r is 0.

m is 0.

n is 1.

z is 1.

R$^{28}$ is halo.

R$^{28}$ is fluoro.

R$^{47}$ is hydroxy.

R$^{57}$ is hydroxy.

One of R$^5$ and R$^6$ is a group of formula (IA) (as depicted above); wherein:

Z is —O— or —S(O)$_b$—; wherein b is 0;

R$^8$ is hydrogen;

R$^9$ is hydrogen;

R$^{10}$ and R$^{11}$ are independently selected from hydrogen or carbocyclyl; wherein R$^{10}$ and R$^{11}$ may be independently optionally substituted on carbon by one or more substituents selected from R$^{28}$;

R$^{13}$ is a group of formula (IB) (as depicted above);

R$^{14}$ is hydrogen;

R$^{15}$ is hydrogen;

R$^{17}$ is C$_{1-10}$alkyl; wherein R$^{17}$ may be optionally substituted on carbon by one or more substituents selected from R$^{47}$; or R$^{17}$ is a group of formula (IC) (as depicted above) wherein:

R$^{18}$ is selected from hydrogen;

R$^{19}$ is selected from hydrogen;

R$^{20}$ is C$_{1-10}$alkyl; wherein R$^{20}$ may be independently optionally substituted on carbon by one or more R$^{57}$;

p is 1;

q is 0;

r is 0;

m is 0;

n is 1;

z is 1; and

R$^{28}$, R$^{47}$ and R$^{57}$ are independently selected from halo and hydroxy.

One of R$^5$ and R$^6$ is a group of formula (IA) (as depicted above); wherein:

Z is —O— or —S(O)$_b$—; wherein b is 0;

R$^8$ is hydrogen;

R$^9$ is hydrogen;

R$^{10}$ and R$^{11}$ are independently selected from hydrogen, phenyl or carbocyclyl; wherein R$^{10}$ and R$^{11}$ may be independently optionally substituted on carbon by one or more substituents selected from halo;

R$^{13}$ is a group of formula (IB) (as depicted above);

R$^{14}$ is hydrogen;

R$^{15}$ is hydrogen;

R$^{17}$ is C$_{1-6}$alkyl; wherein R$^{17}$ may be optionally substituted on carbon by one or more substituents selected from hydroxy; or R$^{17}$ is a group of formula (IC) (as depicted above) wherein:

R$^{18}$ is selected from hydrogen;

R$^{19}$ is selected from hydrogen;

R$^{20}$ is C$_{1-6}$alkyl; wherein R$^{20}$ may be independently optionally substituted on carbon by one or more hydroxy;

p is 1;

q is 0;

r is 0;

m is 0;

n is 1; and z is 1.

One of R$^5$ and R$^6$ is a group of formula (IA) (as depicted above); wherein:

Z is —O— or —S(O)$_b$—; wherein b is 0;

R$^8$ is hydrogen;

R$^9$ is hydrogen;

R$^{10}$ and R$^{11}$ are independently selected from hydrogen, 2-fluorophenyl or carbocyclyl;

R$^{13}$ is a group of formula (IB) (as depicted above);

R$^{14}$ is hydrogen;

R$^{15}$ is hydrogen;

R$^{17}$ is pentyl substituted by 5 hydroxy; or R$^{17}$ is a group of formula (IC) (as depicted above) wherein:

R$^{18}$ is selected from hydrogen;

R$^{19}$ is selected from hydrogen;

R$^{20}$ is pentyl substituted by 5 hydroxy;

p is 1;

q is 0;

r is 0;

m is 0;

n is 1; and z is 1.

Therefore in an further aspect of the invention, there is provided a compound of formula (I) wherein:

$M^1$ is —CH$_2$—;
$M^2$ is —CR$^{22}$R$^{23}$— and —NR$^{24}$—;
R$^{22}$ and R$^{23}$ are independently selected from hydrogen and hydroxy;
R$^1$ and R$^2$ are C$_{1-4}$alkyl;
v is 0;
R$^4$ and R$^7$ are hydrogen;
One of R$^5$ or R$^6$ is selected from a group of formula (IA) (as depicted above) and the other is hydrogen or methylthio;
Z is —O— or —S(O)$_b$—; wherein b is 0;
R$^8$ is hydrogen;
R$^9$ is hydrogen;
R$^{10}$ and R$^{11}$ are independently selected from hydrogen or carbocyclyl; wherein R$^{10}$ and R$^{11}$ may be independently optionally substituted on carbon by one or more substituents selected from R$^{28}$;
R$^{13}$ is a group of formula (IB) (as depicted above);
R$^{14}$ is hydrogen;
R$^{15}$ is hydrogen;
R$^{17}$ is C$_{1-10}$alkyl; wherein R$^{17}$ may be optionally substituted on carbon by one or more substituents selected from R$^{47}$; or R$^{17}$ is a group of formula (IC) (as depicted above) wherein:
R$^{18}$ is selected from hydrogen;
R$^{19}$ is selected from hydrogen;
R$^{20}$ is C$_{1-10}$alkyl; wherein R$^{20}$ may be independently optionally substituted on carbon by one or more R$^{57}$;
p is 1;
q is 0;
r is 0;
m is 0;
n is 1;
z is 1; and
R$^{28}$, R$^{47}$ and R$^{57}$ are independently selected from halo and hydroxy; or a pharmaceutically acceptable salt, solvate, solvate of such a salt or a prodrug thereof.

Therefore in an further aspect of the invention, there is provided a compound of formula (I) wherein:
$M^1$ is —CH$_2$—;
$M^2$is —CR$^{22}$R$^{23}$— and —NR$^{24}$—;
R$^{22}$ and R$^{23}$ are independently selected from hydrogen and hydroxy;
One of R$^1$ and R$^2$ is ethyl and the other is butyl;
v is 0;
R$^4$ and R$^7$ are hydrogen;
One of R$^5$ or R$^6$ is selected from a group of formula (IA) (as depicted above) and the other is hydrogen or methylthio;
Z is —O— or —S(O)$_b$—; wherein b is 0;
R$^8$ is hydrogen;
R$^9$ is hydrogen;
R$^{10}$ and R$^{11}$ are independently selected from hydrogen, 2-fluorophenyl or carbocyclyl;
R$^{13}$ is a group of formula (IB) (as depicted above);
R$^{14}$ is hydrogen;
R$^{15}$ is hydrogen;
R$^{17}$ is pentyl substituted by 5 hydroxy; or R$^{17}$ is a group of formula (IC) (as depicted above) wherein:
R$^{18}$ is selected from hydrogen;
R$^{19}$ is selected from hydrogen;
R$^{20}$ is pentyl substituted by 5 hydroxy;
p is 1;
q is 0;
r is 0;
m is 0;
n is 1; and
z is 1;
or a pharmaceutically acceptable salt, solvate, solvate of such a salt or a prodrug thereof.

In another aspect of the invention, preferred compounds of the invention are any one of the examples or a pharmaceutically acceptable salt, solvate, solvate of such a salt or a prodrug thereof.

Preferred aspects of the invention are those which relate to the compound of formula (I) or a pharmaceutically acceptable salt thereof.

Another aspect of the present invention provides a process for preparing a compound of formula (I) or a pharmaceutically acceptable salt, solvate, solvate of such a salt or a prodrug thereof which process (wherein variable groups are, unless otherwise specified, as defined in formula (I)) comprises of:

Process 1): for compounds of formula (I) wherein Z is —O—, —NR$^a$ or —S—; reacting a compound of formula (IIa) or (IIb):

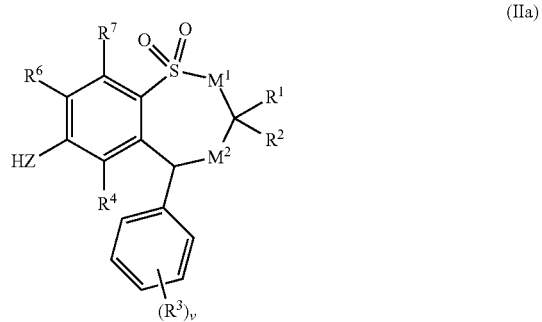

(IIa)

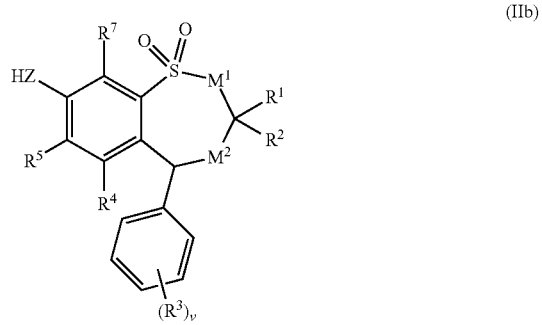

(IIb)

with a compound of formula (III):

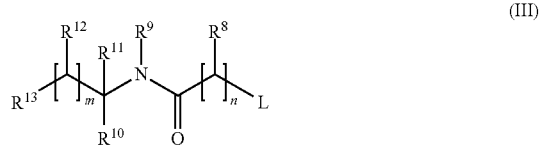

(III)

wherein L is a displaceable group;

Process 2): reacting an acid of formula (IVa) or (IVb):

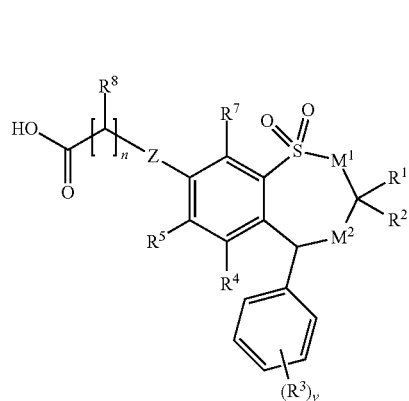

(IVa)

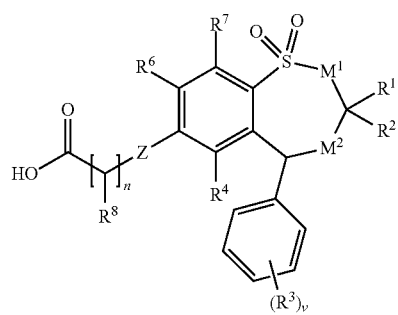

(IVb)

or an activated derivative thereof; with an amine of formula (V):

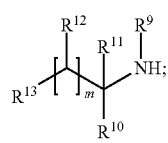

(V)

Process 3): for compounds of formula (I) wherein $R^{13}$ is a group of formula (IB); reacting an acid of formula (VIa):

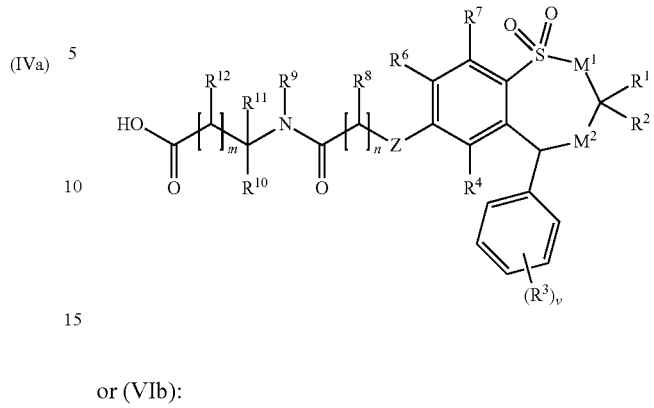

(VIa)

or (VIb):

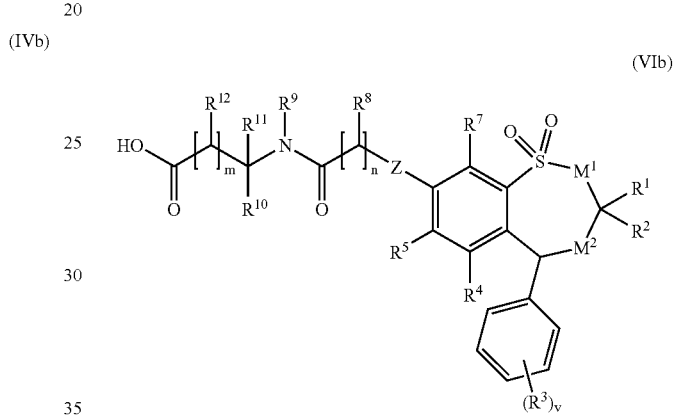

(VIb)

with an amine of formula:

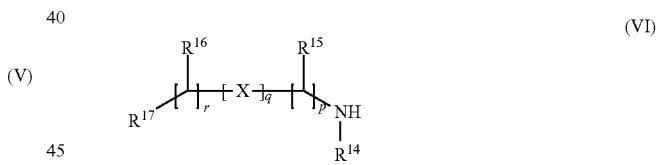

(VI)

Process 4): for compounds of formula (I) wherein $R^{13}$ is a group of formula (IB) and $R^{17}$ is a group of formula (IC); reacting an acid of formula (VIIIa):

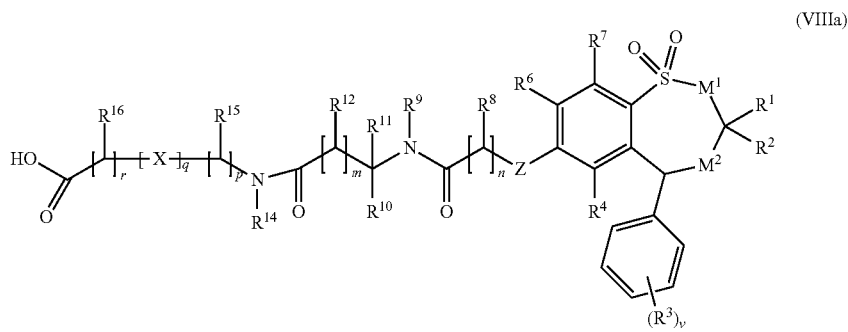

(VIIIa)

or (VIIIb)

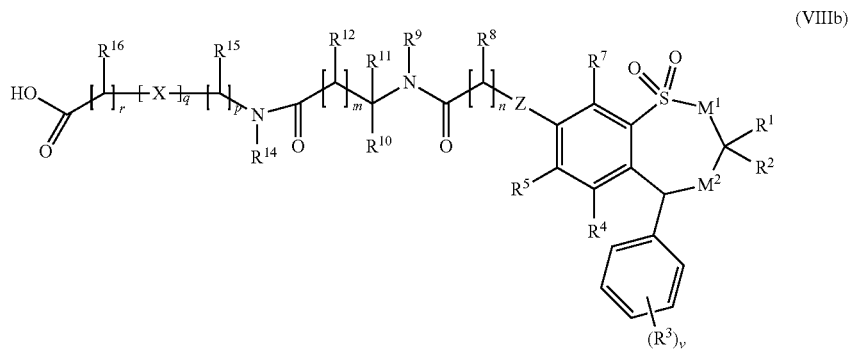

or an activated derivative thereof; with an amine of formula (IX):

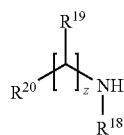

Process 5) for compounds of formula (I) wherein one of $R^5$ and $R^6$ are independently selected from $C_{1-6}$alkylthio optionally substituted on carbon by one or more $R^{25}$; reacting a compound of formula (Xa) or (Xb):

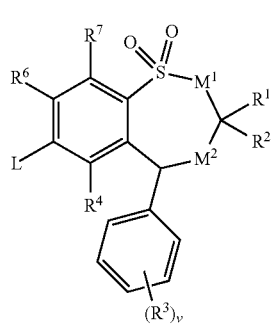

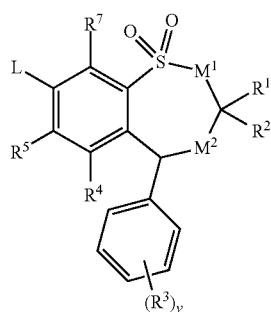

wherein L is a displaceable group; with a thiol of formula (XI):

$$R^m\text{—H} \quad (XI)$$

wherein $R^m$ is $C_{1-6}$alkylthio optionally substituted on carbon by one or more $R^{25}$; and thereafter if necessary or desirable:

i) converting a compound of the formula (I) into another compound of the formula (I);

ii) removing any protecting groups;

iii) forming a pharmaceutically acceptable salt, solvate, solvate of such a salt or a prodrug.

L is a displaceable group, suitable values for L are for example, a halogeno or sulphonyloxy group, for example a chloro, bromo, methanesulphonyloxy or toluene-4-sulphonyloxy group.

Specific reaction conditions for the above reactions are as follows.

The bicyclic ring systems of the present invention may be assembled according to Scheme Ia (1,4-benzothiazepine) or Scheme Ib (benzothiepines) or Scheme IC (1,2-benzothiazepines). The skilled person will appreciate to make any of the above identified intermediates the value of $R^4$ or $R^5$ in the following schemes would be replaced with the appropriate group. For example, to synthesize a compound of formula (IIa) $R^4$ would be HX in the following schemes.

Scheme 1a
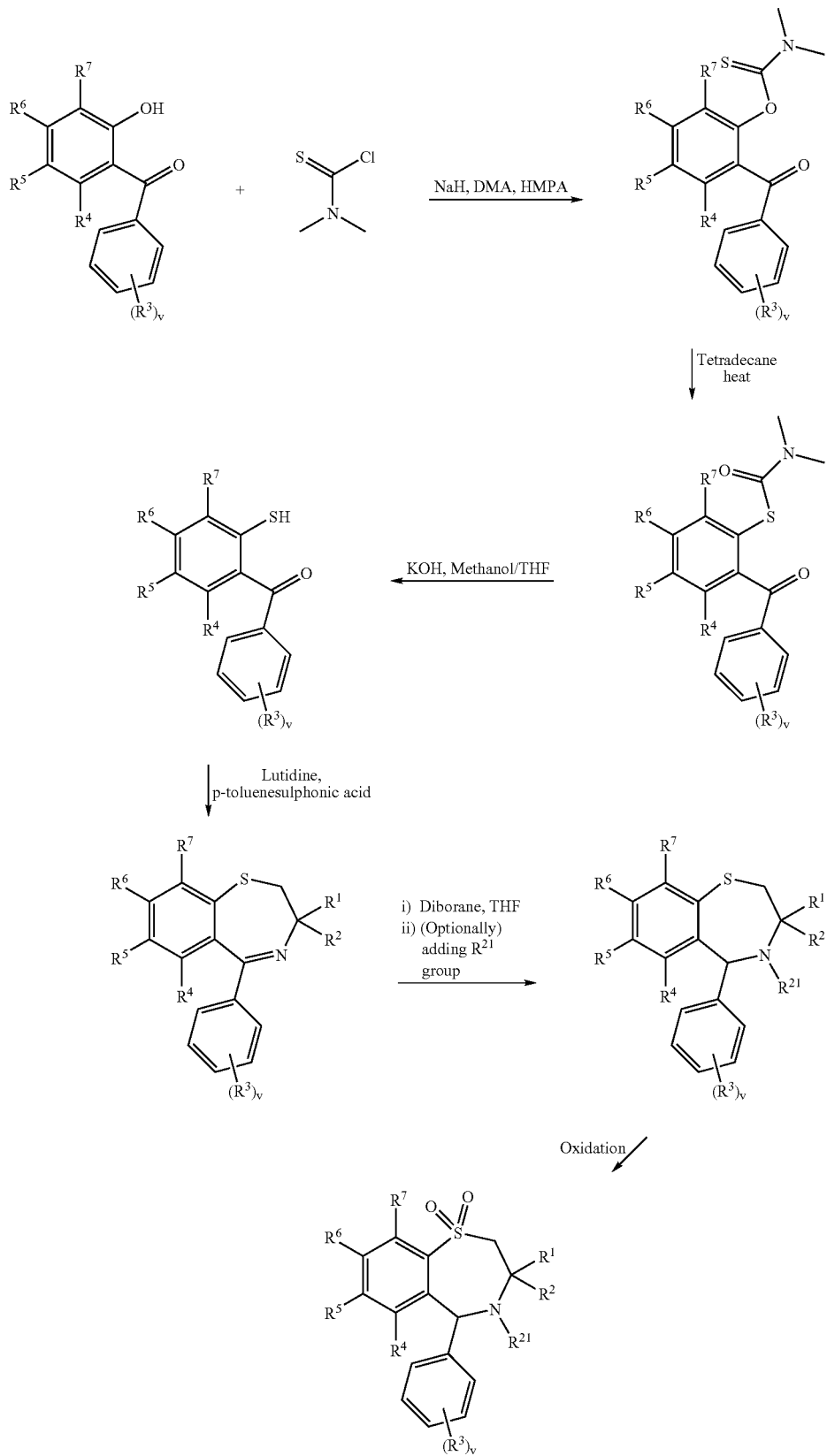

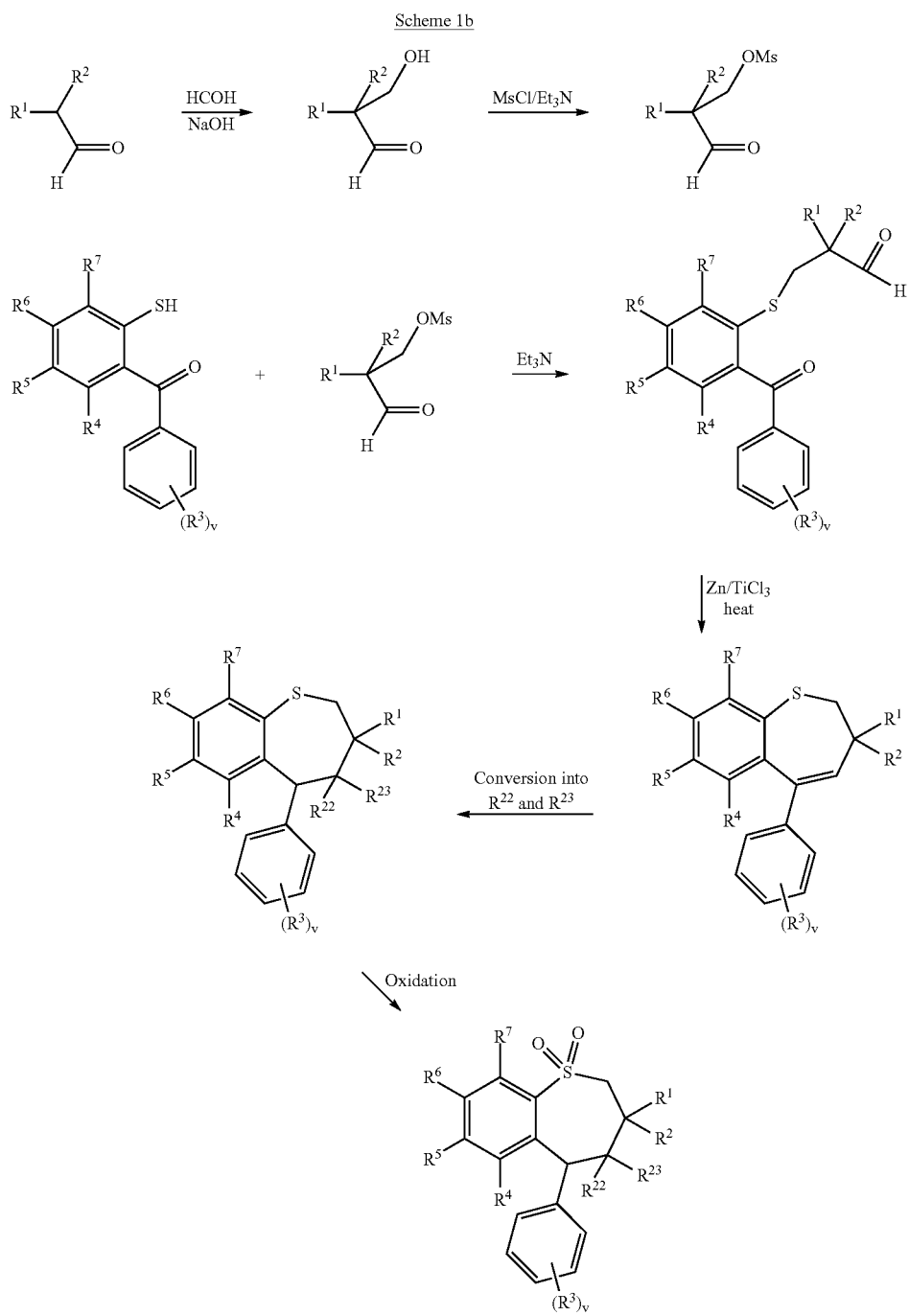
Scheme 1b
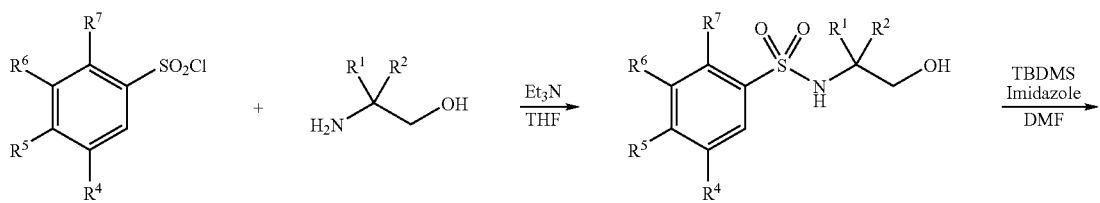
Scheme 1c

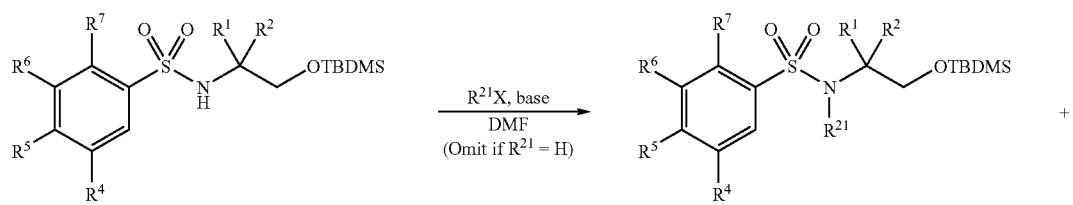
-continued
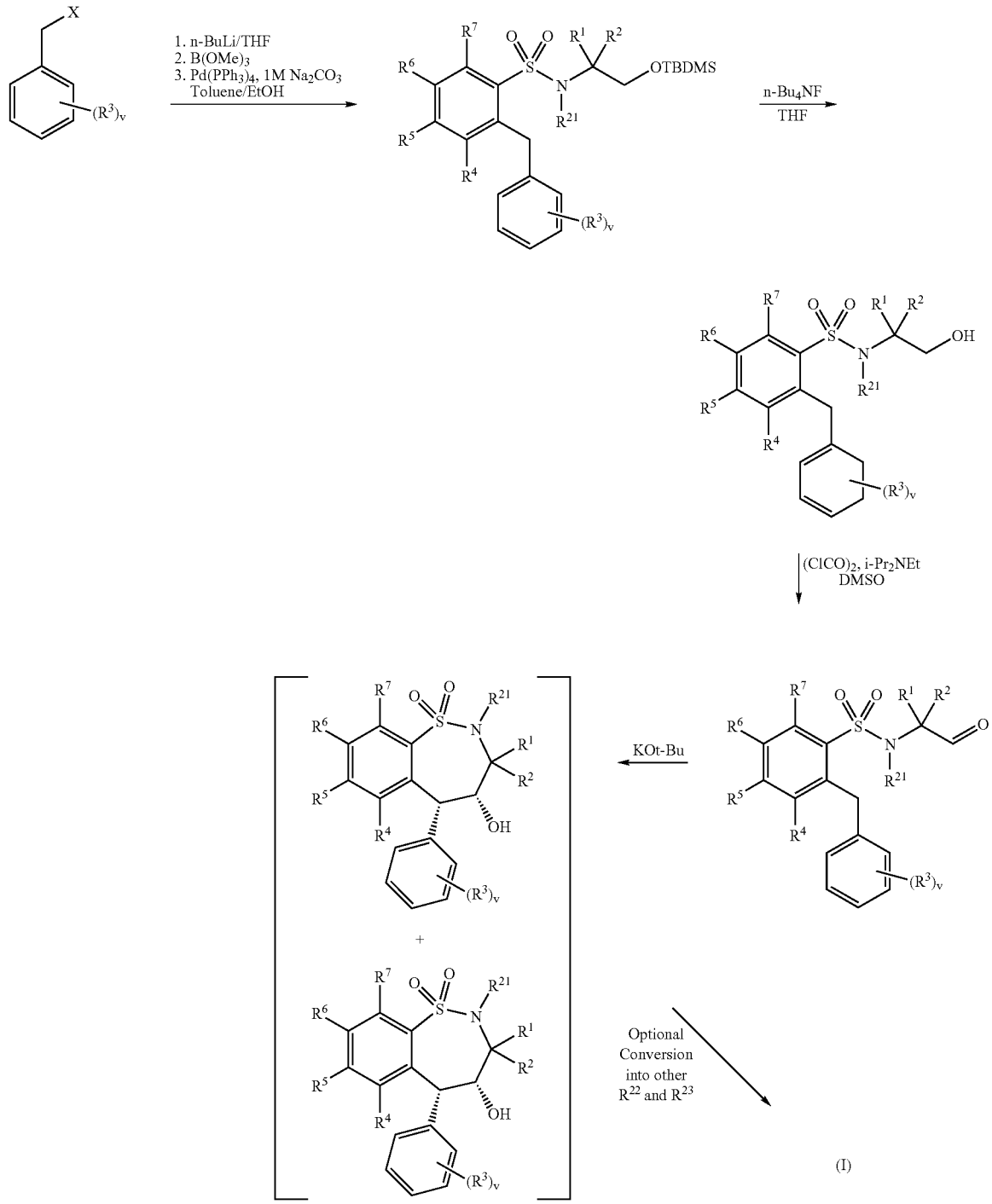

Starting materials for the above schemes are commercially available, or they are known in the literature, or they may be prepared by standard processes known in the art. Process 1): Compounds of formula (IIa) or (IIb) may be reacted with compounds of formula (III) in the presence of a base for example an inorganic base such as sodium carbonate, or an organic base such as Hunigs base, in the presence of a suitable solvent such as acetonitrile, dichloromethane or tetrahydrofuran at a temperature in the range of 0° C. to reflux, preferably at or near reflux.

Compounds of formula (III) are commercially available compounds, or they are known in the literature, or they are prepared by standard processes known in the art. Process 2) and Process 3) and Process 4): Acids and amines may be coupled together in the presence of a suitable coupling reagent. Standard peptide coupling reagents known in the art can be employed as suitable coupling reagents, or for example carbonyldiimidazole and dicyclohexyl-carbodiimide, optionally in the presence of a catalyst such as dimethylaminopyridine or 4-pyrrolidinopyridine, optionally in the presence of a base for example triethylamine, pyridine, or 2,6-di-alkyl-pyridines such as 2,6-lutidine or 2,6-di-tert-butylpyridine. Suitable solvents include dimethylacetamide, dichloromethane, benzene, tetrahydrofuran and dimethylformamide. The coupling reaction may conveniently be performed at a temperature in the range of −40 to 40° C.

Suitable activated acid derivatives include acid halides, for example acid chlorides, and active esters, for example pentafluorophenyl esters. The reaction of these types of compounds with amines is well known in the art, for example they may be reacted in the presence of a base, such as those described above, and in a suitable solvent, such as those described above. The reaction may conveniently be performed at a temperature in the range of −40 to 40° C.

Amines of formula (V), (VII) and (IX) are commercially available, or they are known in the literature, or they may be prepared by standard processes known in the art. Process 4): Compounds of formula (Xa) and (Xb) may be reacted with thiols in the presence of base, for example an inorganic base such as sodium carbonate or an organic base such as Hunigs base, in the presence of a suitable solvent such as DMF or THF at a temperature in the range of 0° C. to reflux.

Compounds of formula (Xa) and (Xb) may be prepared by any of the procedures above for the preparation of compounds of formula (I), but wherein one of $R^4$ and $R^5$ is L.

Compounds of formula (XI) are commercially available compounds, or they are known in the literature, or they are prepared by standard processes known in the art.

It will be appreciated that certain of the various ring substituents in the compounds of the present invention may be introduced by standard aromatic substitution reactions or generated by conventional functional group modifications either prior to or immediately following the processes mentioned above, and as such are included in the process aspect of the invention. Such reactions and modifications include, for example, introduction of a substituent by means of an aromatic substitution reaction, reduction of substituents, alkylation of substituents and oxidation of substituents. The reagents and reaction conditions for such procedures are well known in the chemical art. Particular examples of aromatic substitution reactions include the introduction of a nitro group using concentrated nitric acid, the introduction of an acyl group using, for example, an acyl halide and Lewis acid (such as aluminium trichloride) under Friedel Crafts conditions; the introduction of an alkyl group using an alkyl halide and Lewis acid (such as aluminium trichloride) under Friedel Crafts conditions; and the introduction of a halogeno group. Particular examples of modifications include the reduction of a nitro group to an amino group by for example, catalytic hydrogenation with a nickel catalyst or treatment with iron in the presence of hydrochloric acid with heating; oxidation of alkylthio to alkylsulphinyl or alkylsulphonyl.

It will also be appreciated that in some of the reactions mentioned herein it may be necessary/desirable to protect any sensitive groups in the compounds. The instances where protection is necessary or desirable and suitable methods for protection are known to those skilled in the art.

Conventional protecting groups may be used in accordance with standard practice (for illustration see T.W. Green, Protective Groups in Organic Synthesis, John Wiley and Sons, 1999). Thus, if reactants include groups such as amino, carboxy or hydroxy it may be desirable to protect the group in some of the reactions mentioned herein.

A suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a t-butoxycarbonyl group may be removed, for example, by treatment with a suitable acid as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

The protecting groups may be removed at any convenient stage in the synthesis using conventional techniques well known in the chemical art.

As stated hereinbefore the compounds defined in the present invention possess IBAT inhibitory activity. These properties may be assessed, for example, using an in vitro test assay for studying the effect on bile acid uptake in IBATtransfected cells (Smith L., Price-Jones M. J., Hugnes K. T. and Jones N. R. A.; J Biomolecular Screening, 3, 227-230) or in vivo by studying the effect on radiolabelled bile acid absorption in mice/rats (Lewis M. C., Brieaddy L. E. and Root C., J., J Lip Res 1995, 36, 1098-1105).

According to a further aspect of the invention there is provided a pharmaceutical composition which comprises a compound of formula (I), or a pharmaceutically acceptable salt, solvate, solvate of such a salt or a prodrug thereof, as defined hereinbefore in association with a pharmaceutically-acceptable diluent or carrier.

The composition may be in a form suitable for oral administration, for example as a tablet or capsule, for parenteral injection (including intravenous, subcutaneous, intramuscular, intravascular or infusion) as a sterile solution, suspension or emulsion, for topical administration as an ointment or cream or for rectal administration as a suppository.

In general the above compositions may be prepared in a conventional manner using conventional excipients.

The compound of formula (I), or a pharmaceutically acceptable salt, solvate, solvate of such a salt or a prodrug thereof, will normally be administered to a warm-blooded animal at a unit dose within the range 5-5000 mg per square meter body area of the animal, i.e. approximately 0.02-100 mg/kg, preferably 0.02-50 mg/kg, and this normally provides a therapeutically-effective dose. A unit dose form such as a tablet or capsule will usually contain, for example 1-250 mg of active ingredient. In another aspect of the invention the compound of formula (I), or a pharmaceutically acceptable salt, solvate, solvate of such a salt or a prodrug thereof, will normally be administered to a warm-blooded animal at a unit dose within the range 0.001-20 mg/kg or 0.1-200 mg/day, particularly 1-20 mg/day to provide a therapeutically-effective dose. Preferably a daily dose in the range of 1-50 mg/kg, particularly 0.1-10 mg/kg is employed. In another aspect a daily dose in the rage of 0.02-20 mg/kg is employed. However the daily dose will necessarily be varied depending upon the host treated, the particular route of administration, and the severity of the illness being treated. Accordingly the optimum dosage may be determined by the practitioner who is treating any particular patient.

According to a further aspect of the present invention there is provided a compound of the formula (I), or a pharmaceutically acceptable salt, solvate, solvate of such a salt or a prodrug thereof, as defined hereinbefore for use in a method of prophylactic or therapeutic treatment of a warm-blooded animal, such as man.

We have found that the compounds defined in the present invention, or a pharmaceutically acceptable salt, solvate, solvate of such a salt or a prodrug thereof, are effective IBAT inhibitors, and accordingly have value in the treatment of disease states associated with hyperlipidaemic conditions.

Thus according to this aspect of the invention there is provided a compound of the formula (I), or a pharmaceutically acceptable salt, solvate, solvate of such a salt or a prodrug thereof, as defined hereinbefore for use as a medicament.

According to another feature of the invention there is provided the use of a compound of the formula (I), or a pharmaceutically acceptable salt, solvate, solvate of such a salt or a prodrug thereof, as defined hereinbefore in the manufacture of a medicament for use in the production of an IBAT inhibitory effect in a warm-blooded animal, such as man.

According to another feature of the invention there is provided the use of a compound of the formula (I), or a pharmaceutically acceptable salt, solvate, solvate of such a salt or a prodrug thereof, as defined hereinbefore in the manufacture of a medicament for use in the treatment of hyperlipidaemic conditions in a warm-blooded animal, such as man.

According to another feature of the invention there is provided the use of a compound of the formula (I), or a pharmaceutically acceptable salt, solvate, solvate of such a salt or a prodrug thereof, as defined hereinbefore in the manufacture of a medicament for use in the treatment of dyslipidemic conditions and disorders such as hyperlipidaemia, hypertrigliceridemia, hyperbetalipoproteinemia (high LDL), hyperprebetalipoproteinemia (high VLDL), hyperchylomicronemia, hypolipoproteinemia, hypercholesterolemia, hyperlipoproteinemia and hypoalphalipoproteinemia (low HDL) in a warm-blooded animal, such as man.

According to another feature of the invention there is provided the use of a compound of the formula (I), or a pharmaceutically acceptable salt, solvate, solvate of such a salt or a prodrug thereof, as defined hereinbefore in the manufacture of a medicament for use in the treatment of different clinical conditions such as atherosclerosis, arteriosclerosis, arrhythmia, hyper-thrombotic conditions, vascular dysfunction, endothelial dysfunction, heart failure, coronary heart diseases, cardiovascular diseases, myocardial infarction, angina pectoris, peripheral vascular diseases, inflammation of cardiovascular tissues such as heart, valves, vasculature, arteries and veins, aneurisms, stenosis, restenosis, vascular plaques, vascular fatty streaks, leukocytes, monocytes and/or macrophage infiltration, intimal thickening, medial thinning, infectious and surgical trauma and vascular thrombosis, stroke and transient ischaemic attacks in a warm-blooded animal, such as man.

According to another feature of the invention there is provided the use of a compound of the formula (I), or a pharmaceutically acceptable salt, solvate, solvate of such a salt or a prodrug thereof, as defined hereinbefore in the manufacture of a medicament for use in the treatment of atherosclerosis, coronary heart diseases, myocardial infarction, angina pectoris, peripheral vascular diseases, stroke and transient ischaemic attacks in a warm-blooded animal, such as man.

According to a further feature of this aspect of the invention there is provided a method for producing an IBAT inhibitory effect in a warm-blooded animal, such as man, in need of such treatment which comprises administering to said animal an effective amount of a compound of formula (I), or a pharmaceutically acceptable salt, solvate, solvate of such a salt or a prodrug thereof.

According to a further feature of this aspect of the invention there is provided a method of treating hyperlipidemic conditions in a warm-blooded animal, such as man, in need of such treatment which comprises administering to said animal an effective amount of a compound of formula (I), or a pharmaceutically acceptable salt, solvate, solvate of such a salt or a prodrug thereof.

According to a further feature of this aspect of the invention there is provided a method of treating dyslipidemic conditions and disorders such as hyperlipidaemia, hypertrigliceridemia, hyperbetalipoproteinemia (high LDL), hyperprebetalipoproteinemia (high VLDL), hyperchylomicronemia, hypolipoproteinemia, hypercholesterolemia, hyperlipoproteinemia and hypoalphalipoproteinemia (low HDL) in a warm-blooded animal, such as man, in need of such treatment which comprises administering to said animal an effective amount of a compound of formula (I), or a pharmaceutically acceptable salt, solvate, solvate of such a salt or a prodrug thereof.

According to a further feature of this aspect of the invention there is provided a method of treating different clinical conditions such as atherosclerosis, arteriosclerosis, arrhythmia, hyper-thrombotic conditions, vascular dysfunction, endothelial dysfunction, heart failure, coronary heart diseases, cardiovascular diseases, myocardial infarction, angina pectoris, peripheral vascular diseases, inflammation of cardiovascular tissues such as heart, valves, vasculature, arteries and veins, aneurisms, stenosis, restenosis, vascular plaques, vascular fatty streaks, leukocytes, monocytes and/or macrophage infiltration, intimal thickening, medial thinning, infectious and surgical trauma and vascular thrombosis, stroke and transient ischaemic attacks in need of such treatment which comprises administering to said animal an effective amount of a compound of formula (I), or a pharmaceutically acceptable salt, solvate, solvate of such a salt or a prodrug thereof.

According to a further feature of this aspect of the invention there is provided a method of treating atherosclerosis, coronary heart diseases, myocardial infarction, angina pectoris, peripheral vascular diseases, stroke and transient ischaemic attacks in a warm-blooded animal, such as man, in need of such treatment which comprises administering to said animal an effective amount of a compound of formula (I), or a pharmaceutically acceptable salt, solvate, solvate of such a salt or a prodrug thereof.

There is evidence that an IBAT inhibitor might potentially be useful in the treatment and/or prevention of gallstones. According to a further feature of this aspect of the invention there is provided a method of treating and/or preventing gallstones in a warm-blooded animal, such as man, in need of such treatment which comprises administering to said animal an effective amount of a compound of formula (I), or a pharmaceutically acceptable salt, solvate, solvate of such a salt or a prodrug thereof.

The size of the dose required for the therapeutic or prophylactic treatment will necessarily be varied depending on the host treated, the route of administration and the severity of the illness being treated. A unit dose in the range, for example, 0.1-50 mg/kg preferably 0.1-10 mg/kg is envisaged.

The IBAT inhibitory activity defined hereinbefore may be applied as a sole therapy or may involve, in addition to a compound of the invention, one or more other substances and/or treatments. Such conjoint treatment may be achieved by way of the simultaneous, sequential or separate administration of the individual components of the treatment. According to this aspect of the invention there is provided a pharmaceutical product comprising a compound of the formula (I), or a pharmaceutically acceptable salt, solvate, solvate of such a salt or a prodrug thereof, as defined hereinbefore and an additional IBAT inhibitory substance as defined hereinbefore and an additional hypolipidaemic agent for the conjoint treatment of hyperlipidaemia.

In another aspect of the invention, the compound of formula (I), or a pharmaceutically acceptable salt, solvate, solvate of such a salt or a prodrug thereof, may be administered in association with an HMG Co-A reductase inhibitor, or pharmaceutically acceptable salts, solvates, solvates of such salts or prodrugs thereof. Suitable HMG Co-A reductase inhibitors, pharmaceutically acceptable salts, solvates, solvates of such salts or prodrugs thereof are statins well known in the art. Particular statins are fluvastatin, lovastatin, pravastatin, simvastatin, atorvastatin, cerivastatin, bervastatin, dalvastatin, mevastatin and (E)-7-[4-(4-fluorophenyl)-6-isopropyl-2-[methyl(methylsulphonyl)amino]pyrimidin-5-yl](3R,5S)-3,5-dihydroxyhept-6-enoic acid (rosuvastatin), or a pharmaceutically acceptable salt, solvate, solvate of such a salt or a prodrug thereof. A particular statin is atorvastatin, or a pharmaceutically acceptable salt, solvate, solvate of such a salt or a prodrug thereof. A more particular statin is atorvastatin calcium salt. A further particular statin is (E)-7-[4-(4-fluorophenyl)-6-isopropyl-2-[methyl(methylsulphonyl)amino]pyrimidin-5-yl](3R,5S)-3,5-dihydroxyhept-6-enoic acid (rosuvastatin), or a pharmaceutically acceptable salt, solvate, solvate of such a salt or a prodrug thereof. A preferable particular statin is rosuvastatin calcium salt.

Therefore in an additional feature of the invention, there is provided a combination of a compound of formula (I), or a pharmaceutically acceptable salt, solvate, solvate of such a salt or a prodrug thereof and an HMG Co-A reductase inhibitor, or a pharmaceutically acceptable salt, solvate, solvate of such a salt or a prodrug thereof.

In an additional aspect of the invention, the compound of formula (I), or a pharmaceutically acceptable salt, solvate, solvate of such a salt or a prodrug thereof may be administered in association with an HMG Co-A reductase inhibitor, or a pharmaceutically acceptable salt, solvate, solvate of such a salt or a prodrug thereof, and/or a bile acid binder thereby avoiding a possible risk of excess of bile acids in colon caused by the inhibition of the ileal bile acid transport system. An excess of bile acids in the visceral contents may cause diarrhoea. Thus, the present invention also provides a treatment of a possible side effect such as diarrhoea in patients during therapy comprising the compound of formula (I), or a pharmaceutically acceptable salt, solvate, solvate of such a salt or a prodrug thereof.

An HMG CoA-reductase inhibitor, or a pharmaceutically acceptable salt, solvate, solvate of such a salt or a prodrug thereof will by its action decrease the endogenous cholesterol available for the bile acid synthesis and have an additive effect in combination with the compound of formula (I), or a pharmaceutically acceptable salt, solvate, solvate of such a salt or a prodrug thereof on lipid lowering.

Suitable bile acid binders for such a combination therapy are resins, such as cholestyramine and cholestipol. One advantage is that the dose of bile acid binder might be kept lower than the therapeutic dose for treatment of cholesterolaemia in single treatment comprising solely a bile acid binder. By a low dose of bile acid binder any possible side effects caused by poor tolerance of the patient to the therapeutic dose could also be avoided.

Therefore in an additional feature of the invention, there is provided a combination of a compound of formula (I), or a pharmaceutically acceptable salt, solvate, solvate of such a salt or a prodrug thereof and a bile acid binder.

Therefore in an additional feature of the invention, there is provided a method for producing an IBAT inhibitory effect in a warm-blooded animal, such as man, in need of such treatment which comprises administering to said animal an effective amount of a compound of formula (I), or a pharmaceutically acceptable salt, solvate, solvate of such a salt or a prodrug thereof in simultaneous, sequential or separate administration with an effective amount of an HMG Co-A reductase inhibitor, or a pharmaceutically acceptable salt, solvate, solvate of such a salt or a prodrug thereof.

Therefore in an additional feature of the invention, there is provided a method for producing an IBAT inhibitory effect in a warm-blooded animal, such as man, in need of such treatment which comprises administering to said animal an effective amount of a compound of formula (I), or a pharmaceutically acceptable salt, solvate, solvate of such a salt or a prodrug thereof in simultaneous, sequential or separate administration with a bile acid binder.

Therefore in an additional feature of the invention, there is provided a method for producing an IBAT inhibitory effect in a warm-blooded animal, such as man, in need of such treatment which comprises administering to said animal an effective amount of a compound of formula (I), or a pharmaceutically acceptable salt, solvate, solvate of such a salt or a prodrug thereof in simultaneous, sequential or separate administration with an effective amount of an HMG Co-A reductase inhibitor, or a pharmaceutically acceptable salt, solvate, solvate of such a salt or a prodrug thereof, in simultaneous, sequential or separate administration with a bile acid binder.

Therefore in an additional feature of the invention, there is provided a method of treating hyperlipidemic conditions in a warm-blooded animal, such as man, in need of such treatment which comprises administering to said animal an effective amount of a compound of formula (I), or a pharmaceutically acceptable salt, solvate, solvate of such a salt or a prodrug thereof in simultaneous, sequential or separate administration with an effective amount of an HMG Co-A reductase inhibitor, or a pharmaceutically acceptable salt, solvate, solvate of such a salt or a prodrug thereof.

Therefore in an additional feature of the invention, there is provided a method of treating hyperlipidemic conditions in a warm-blooded animal, such as man, in need of such treatment which comprises administering to said animal an effective amount of a compound of formula (I), or a pharmaceutically acceptable salt, solvate, solvate of such a salt or a prodrug thereof in simultaneous, sequential or separate administration with an effective amount of a bile acid binder.

Therefore in an additional feature of the invention, there is provided a method of treating hyperlipidemic conditions in a warm-blooded animal, such as man, in need of such treatment which comprises administering to said animal an effective amount of a compound of formula (I), or a pharmaceutically acceptable salt, solvate, solvate of such a salt or a prodrug thereof in simultaneous, sequential or separate administration with an effective amount of an HMG Co-A reductase inhibitor, or a pharmaceutically acceptable salt, solvate, solvate of such a salt or a prodrug thereof, in simultaneous, sequential or separate administration with a bile acid binder.

According to a further aspect of the invention there is provided a pharmaceutical composition which comprises a compound of formula (I), or a pharmaceutically acceptable salt, solvate, solvate of such a salt or a prodrug thereof, and an HMG Co-A reductase inhibitor, or a pharmaceutically acceptable salt, solvate, solvate of such a salt or a prodrug thereof, in association with a pharmaceutically acceptable diluent or carrier.

According to a further aspect of the invention there is provided a pharmaceutical composition which comprises a compound of formula (I), or a pharmaceutically acceptable salt, solvate, solvate of such a salt or a prodrug thereof, and a bile acid binder, in association with a pharmaceutically acceptable diluent or carrier.

According to a further aspect of the invention there is provided a pharmaceutical composition which comprises a compound of formula (I), or a pharmaceutically acceptable salt, solvate, solvate of such a salt or a prodrug thereof, and an HMG Co-A reductase inhibitor, or a pharmaceutically acceptable salt, solvate, solvate of such a salt or a prodrug thereof, and a bile acid binder in association with a pharmaceutically acceptable diluent or carrier.

According to a further aspect of the present invention there is provided a kit comprising a compound of formula (I), or a pharmaceutically acceptable salt, solvate, solvate of such a salt or a prodrug thereof, and an HMG Co-A reductase inhibitor, or a pharmaceutically acceptable salt, solvate, solvate of such a salt or a prodrug thereof.

According to a further aspect of the present invention there is provided a kit comprising a compound of formula (I), or a pharmaceutically acceptable salt, solvate, solvate of such a salt or a prodrug thereof, and a bile acid binder.

According to a further aspect of the present invention there is provided a kit comprising a compound of formula (I), or a pharmaceutically acceptable salt, solvate, solvate of such a salt or a prodrug thereof, and an HMG Co-A reductase inhibitor, or a pharmaceutically acceptable salt, solvate, solvate of such a salt or a prodrug thereof and a bile acid binder.

According to a further aspect of the present invention there is provided a hit comprising:
a) a compound of formula (I), or a pharmaceutically acceptable salt, solvate, solvate of such a salt or a prodrug thereof, in a first unit dosage form;
b) an HMG Co-A reductase inhibitor, or a pharmaceutically acceptable salt, solvate, solvate of such a salt or a prodrug thereof; in a second unit dosage form; and
c) container means for containing said first and second dosage forms.

According to a further aspect of the present invention there is provided a kit comprising:
a) a compound of formula (I), or a pharmaceutically acceptable salt, solvate, solvate of such a salt or a prodrug thereof, in a first unit dosage form;
b) a bile acid binder; in a second unit dosage form; and
c) container means for containing said first and second dosage forms.

According to a further aspect of the present invention there is provided a kit comprising:
a) a compound of formula (I), or a pharmaceutically acceptable salt, solvate, solvate of such a salt or a prodrug thereof, in a first unit dosage form;
b) an HMG Co-A reductase inhibitor, or a pharmaceutically acceptable salt, solvate, solvate of such a salt or a prodrug thereof; in a second unit dosage form;
c) a bile acid binder; in a third unit dosage form; and
d) container means for containing said first, second and third dosage forms.

According to a further aspect of the present invention there is provided a kit comprising:
a) a compound of formula (I), or a pharmaceutically acceptable salt, solvate, solvate of such a salt or a prodrug thereof, together with a pharmaceutically acceptable diluent or carrier, in a first unit dosage form;
b) an HMG Co-A reductase inhibitor, or a pharmaceutically acceptable salt, solvate, solvate of such a salt or a prodrug thereof, in a second unit dosage form; and
c) container means for containing said first and second dosage forms.

According to a further aspect of the present invention there is provided a kit comprising:
a) a compound of formula (I), or a pharmaceutically acceptable salt, solvate, solvate of such a salt or a prodrug thereof, together with a pharmaceutically acceptable diluent or carrier, in a first unit dosage form;
b) a bile acid binder, in a second unit dosage form; and
c) container means for containing said first and second dosage forms.

According to a further aspect of the present invention there is provided a kit comprising:
a) a compound of formula (I), or a pharmaceutically acceptable salt, solvate, solvate of such a salt or a prodrug thereof, together with a pharmaceutically acceptable diluent or carrier, in a first unit dosage form;

b) an HMG Co-A reductase inhibitor, or a pharmaceutically acceptable salt, solvate, solvate of such a salt or a prodrug thereof, in a second unit dosage form; and c) a bile acid binder; in a third unit dosage form; and d) container means for containing said first, second and third dosage forms.

According to another feature of the invention there is provided the use of a compound of the formula (I), or a pharmaceutically acceptable salt, solvate, solvate of such a salt or a prodrug thereof, and an HMG Co-A reductase inhibitor, or a pharmaceutically acceptable salt, solvate, solvate of such a salt or a prodrug thereof, in the manufacture of a medicament for use in the production of an IBAT inhibitory effect in a warm-blooded animal, such as man.

According to another feature of the invention there is provided the use of a compound of the formula (I), or a pharmaceutically acceptable salt, solvate, solvate of such a salt or a prodrug thereof, and a bile acid binder, in the manufacture of a medicament for use in the production of an IBAT inhibitory effect in a warm-blooded animal, such as man.

According to another feature of the invention there is provided the use of a compound of the formula (I), or a pharmaceutically acceptable salt, solvate, solvate of such a salt or a prodrug thereof, and an HMG Co-A reductase inhibitor, or a pharmaceutically acceptable salt, solvate, solvate of such a salt or a prodrug thereof, and a bile acid binder, in the manufacture of a medicament for use in the production of an IBAT inhibitory effect in a warm-blooded animal, such as man.

According to another feature of the invention there is provided the use of a compound of the formula (I), or a pharmaceutically acceptable salt, solvate, solvate of such a salt or a prodrug thereof, an HMG Co-A reductase inhibitor, or a pharmaceutically acceptable salt, solvate, solvate of such a salt or a prodrug thereof, in the manufacture of a medicament for use in the treatment of hyperlipidaemic conditions in a warm-blooded animal, such as man.

According to another feature of the invention there is provided the use of a compound of the formula (I), or a pharmaceutically acceptable salt, solvate, solvate of such a salt or a prodrug thereof, a bile acid binder, in the manufacture of a medicament for use in the treatment of hyperlipidaemic conditions in a warm-blooded animal, such as man.

According to another feature of the invention there is provided the use of a compound of the formula (I), or a pharmaceutically acceptable salt, solvate, solvate of such a salt or a prodrug thereof, an HMG Co-A reductase inhibitor, or a pharmaceutically acceptable salt, solvate, solvate of such a salt or a prodrug thereof, and a bile acid binder, in the manufacture of a medicament for use in the treatment of hyperlipidaemic conditions in a warm-blooded animal, such as man.

According to a further aspect of the present invention there is provided a combination treatment comprising the administration of an effective amount of a compound of the formula (I), or a pharmaceutically acceptable salt, solvate, solvate of such a salt or a prodrug thereof, optionally together with a pharmaceutically acceptable diluent or carrier, with the simultaneous, sequential or separate administration of an effective amount of an HMG Co-A reductase inhibitor, or a pharmaceutically acceptable salt, solvate, solvate of such a salt or a prodrug thereof, optionally together with a pharmaceutically acceptable diluent or carrier to a warm-blooded animal, such as man in need of such therapeutic treatment.

According to a further aspect of the present invention there is provided a combination treatment comprising the administration of an effective amount of a compound of the formula (I), or a pharmaceutically acceptable salt, solvate, solvate of such a salt or a prodrug thereof, optionally together with a pharmaceutically acceptable diluent or carrier, with the simultaneous, sequential or separate administration of an effective amount of a bile acid binder, optionally together with a pharmaceutically acceptable diluent or carrier to a warm-blooded animal, such as man in need of such therapeutic treatment.

According to a further aspect of the present invention there is provided a combination treatment comprising the administration of an effective amount of a compound of the formula (I), or a pharmaceutically acceptable salt, solvate, solvate of such a salt or a prodrug thereof, optionally together with a pharmaceutically acceptable diluent or carrier, with the simultaneous, sequential or separate administration of an effective amount of an HMG Co-A reductase inhibitor, or a pharmaceutically acceptable salt, solvate, solvate of such a salt or a prodrug thereof, optionally together with a pharmaceutically acceptable excipient, with the simultaneous, sequential or separate administration of an effective amount of a bile acid binder, optionally together with a pharmaceutically acceptable diluent or carrier to a warm-blooded animal, such as man in need of such therapeutic treatment.

According to an additional further aspect of the present invention there is provided a combination treatment comprising the administration of an effective amount of a compound of the formula (I), or a pharmaceutically acceptable salt, solvate, solvate of such a salt or a prodrug thereof, optionally together with a pharmaceutically acceptable diluent or carrier, with the simultaneous, sequential or separate administration one or more of the following agents selected from Group X:

a CETP (cholesteryl ester transfer protein) inhibitor, for example those referenced and described in WO 00/38725 page 7 line 22-page 10, line 17 which are incorporated herein by reference;

a cholesterol absorption antagonist for example azetidinones such as SCH 58235 and those described in U.S. Pat. No. 5,767,115 which are incorporated herein by reference;

a MTP (microsomal transfer protein) inhibitor for example those described in Science, 282, 751-54, 1998 which are incorporated herein by reference;

a fibric acid derivative; for example clofibrate, gemfibrozil, fenofibrate, ciprofibrate and bezafibrate;

a nicotinic acid derivative, for example, nicotinic acid (niacin), acipimox and niceritrol;

a phytosterol compound for example stanols;

probucol;

an anti-obesity compound for example orlistat (EP 129, 748) and sibutramine (GB 2,184,122 and U.S. Pat. No. 4,929,629);

an antihypertensive compound for example an angiotensin converting enzyme inhibitor, an angiotensin II receptor antagonist, an andrenergic blocker, an alpha andrenergic blocker, a beta andrenergic blocker, a mixed alpha/beta andrenergic blocker, an andrenergic stimulant, calcium channel blocker, a diuretic or a vasodilator;

insulin;

sulphonylureas including glibenclamide, tolbutamide;

metformin; and/or acarbose;

or a pharmaceutically acceptable salt, solvate, solvate of such a salt or a prodrug thereof, optionally together with a pharmaceutically acceptable diluent or carrier to a warm-blooded animal, such as man in need of such therapeutic treatment.

Particular ACE inhibitors or pharmaceutically acceptable salts, solvates, solvate of such salts or a prodrugs thereof, including active metabolites, which can be used in combination with a compound of formula (I) include but are not limited to, the following compounds: alacepril, alatriopril, altiopril calcium, ancovenin, benazepril, benazepril hydrochloride, benazeprilat, benzoylcaptopril, captopril, captopril-cysteine, captopril-glutathione, ceranapril, ceranopril, ceronapril, cilazapril, cilazaprilat, delapril, delapril-diacid, enalapril, enalaprilat, enapril, epicaptopril, foroxymithine, fosfenopril, fosenopril, fosenopril sodium, fosinopril, fosinopril sodium, fosinoprilat, fosinoprilic acid, glycopril, hemorphin-4, idrapril, imidapril, indolapril, indolaprilat, libenzapril, lisinopril, lyciumin A, lyciumin B, mixanpril, moexipril, moexiprilat, moveltipril, muracein A, muracein B, muracein C, pentopril, perindopril, perindoprilat, pivalopril, pivopril, quinapril, quinapril hydrochloride, quinaprilat, ramipril, ramiprilat, spirapril, spirapril hydrochloride, spiraprilat, spiropril, spiropril hydrochloride, temocapril, temocapril hydrochloride, teprotide, trandolapril, trandolaprilat, utibapril, zabicipril, zabiciprilat, zofenopril and zofenoprilat. Preferred ACE inhibitors for use in the present invention are ramipril, ramiprilat, lisinopril, enalapril and enalaprilat. More preferred ACE inhibitors for uses in the present invention are ramipril and ramiprilat.

Preferred angiotensin II antagonists, pharmaceutically acceptable salts, solvates, solvate of such salts or a prodrugs thereof for use in combination with a compound of formula (I) include, but are not limited to, compounds: candesartan, candesartan cilexetil, losartan, valsartan, irbesartan, tasosartan, telmisartan and eprosartan. Particularly preferred angiotensin II antagonists or pharmaceutically acceptable derivatives thereof for use in the present invention are candesartan and candesartan cilexetil.

Therefore, in an additional feature of the invention, there is provided a combination of a compound of formula (I), or a pharmaceutically acceptable salt, solvate, solvate of such a salt or a prodrug thereof and a compound from Group X or a pharmaceutically acceptable salt, solvate, solvate of such a salt or a prodrug thereof.

Therefore in an additional feature of the invention, there is provided a method of treating hyperipidaernic conditions in a warmblooded animal, such as man, in need of such treatment which comprises administering to said animal an effective amount of a compound of formula (I), or a pharmaceutically acceptable salt, solvate, solvate of such a salt or a prodrug thereof in simultaneous, sequential or separate administration with an effective amount of a compound from Group X, or a pharmaceutically acceptable salt, solvate, solvate of such a salt or a prodrug thereof.

According to a further aspect of the invention there is provided a pharmaceutical composition which comprises a compound of formula (I), or a pharmaceutically acceptable salt, solvate, solvate of such a salt or a prodrug thereof, and a compound from Group X, or a pharmaceutically acceptable salt, solvate, solvate of such a salt or a prodrug thereof, in association with a pharmaceutically acceptable diluent or carrier.

According to another feature of the invention there is provided the use of a compound of the formula (I), or a pharmaceutically acceptable salt, solvate, solvate of such a salt or a prodrug thereof, and a compound from Group X, or a pharmaceutically acceptable salt, solvate, solvate of such a salt or a prodrug thereof, in the manufacture of a medicament for use in the treatment of hyperlipidaemic conditions in a warm-blooded animal, such as man.

In another aspect of the invention, the compound of formula (I), or a pharmaceutically acceptable salt, solvate, solvate of such a salt or a prodrug thereof, may be administered in association with a PPAR alpha and/or gamma agonist, or pharmaceutically acceptable salts, solvates, solvates of such salts or prodrugs thereof. Suitable PPAR alpha and/or gamma agonists, pharmaceutically acceptable salts, solvates, solvates of such salts or prodrugs thereof are well known in the art. These include the compounds described in WO 01/12187, WO 01/12612, WO 99/62870, WO 99/62872, WO 99/62871, WO 98/57941, WO 01/40170, J Med Chem, 1996, 39, 665, Expert Opinion on Therapeutic Patents, 10 (5), 623-634 (in particular the compounds described in the patent applications listed on page 634) and J Med Chem, 2000, 43, 527 which are all incorporated herein by reference. Particularly a PPAR alpha and/or gamma agonist refers to WY-14643, clofibrate, fenofibrate, bezafibrate, GW 9578, troglitazone, pioglitazone, rosiglitazone, eglitazone, proglitazone, BRL-49634, KRP-297, JTT-501, SB 213068, GW 1929, GW 7845, GW 0207, L-796449, L-165041 and GW 2433. Particularly a PPAR alpha and/or gamma agonist refers to (S)-2-ethoxy-3-[4-(2-{4-methanesulphonyloxyphenyl}ethoxy)phenyl]propanoic acid and pharmaceutically acceptable salts thereof. Additional suitable PPAR alpha and/or gamma agonists are NN622/Ragaglitazar and BMS 298585.

Therefore in an additional feature of the invention, there is provided a combination of a compound of formula (I), or a pharmaceutically acceptable salt, solvate, solvate of such a salt or a prodrug thereof and a PPAR alpha and/or gamma agonist, or a pharmaceutically acceptable salt, solvate, solvate of such a salt or a prodrug thereof.

Therefore in an additional feature of the invention, there is provided a method for producing an IBAT inhibitory effect in a warm-blooded animal, such as man, in need of such treatment which comprises administering to said animal an effective amount of a compound of formula (I), or a pharmaceutically acceptable salt, solvate, solvate of such a salt or a prodrug thereof in simultaneous, sequential or separate administration with an effective amount of a PPAR alpha and/or gamma agonist, or a pharmaceutically acceptable salt, solvate, solvate of such a salt or a prodrug thereof.

Therefore in an additional feature of the invention, there is provided a method of treating hyperlipidemic conditions in a warm-blooded animal, such as man, in need of such treatment which comprises administering to said animal an effective amount of a compound of formula (I), or a pharmaceutically acceptable salt, solvate, solvate of such a salt or a prodrug thereof in simultaneous, sequential or separate administration with an effective amount of a PPAR alpha and/or gamma agonist, or a pharmaceutically acceptable salt, solvate, solvate of such a salt or a prodrug thereof.

According to a further aspect of the invention there is provided a pharmaceutical composition which comprises a compound of formula (I), or a pharmaceutically acceptable salt, solvate, solvate of such a salt or a prodrug thereof, and a PPAR alpha and/or gamma agonist, or a pharmaceutically acceptable salt, solvate, solvate of such a salt or a prodrug thereof, in association with a pharmaceutically acceptable diluent or carrier.

According to a further aspect of the present invention there is provided a kit comprising a compound of formula (I), or a pharmaceutically acceptable salt, solvate, solvate of such a salt or a prodrug thereof, and a PPAR alpha and/or gamma agonist, or a pharmaceutically acceptable salt, solvate, solvate of such a salt or a prodrug thereof.

According to a further aspect of the present invention there is provided a kit comprising:
a) a compound of formula (I), or a pharmaceutically acceptable salt, solvate, solvate of such a salt or a prodrug thereof, in a first unit dosage form;

b) a PPAR alpha and/or gamma agonist, or a pharmaceutically acceptable salt, solvate, solvate of such a salt or a prodrug thereof; in a second unit dosage form; and c) container means for containing said first and second dosage forms.

According to a further aspect of the present invention there is provided a kit comprising:

a) a compound of formula (I), or a pharmaceutically acceptable salt, solvate, solvate of such a salt or a prodrug thereof, together with a pharmaceutically acceptable diluent or carrier, in a first unit dosage form;

b) a PPAR alpha and/or gamma agonist, or a pharmaceutically acceptable salt, solvate, solvate of such a salt or a prodrug thereof, in a second unit dosage form; and c) container means for containing said first and second dosage forms.

According to another feature of the invention there is provided the use of a compound of the formula (I), or a pharmaceutically acceptable salt, solvate, solvate of such a salt or a prodrug thereof, and a PPAR alpha and/or gamma agonist, or a pharmaceutically acceptable salt, solvate, solvate of such a salt or a prodrug thereof, in the manufacture of a medicament for use in the production of an IBAT inhibitory effect in a warm-blooded animal, such as man.

According to another feature of the invention there is provided the use of a compound of the formula (I), or a pharmaceutically acceptable salt, solvate, solvate of such a salt or a prodrug thereof, a PPAR alpha and/or gamma agonist, or a pharmaceutically acceptable salt, solvate, solvate of such a salt or a prodrug thereof, in the manufacture of a medicament for use in the treatment of hyperlipidaemic conditions in a warm-blooded animal, such as man.

According to a further aspect of the present invention there is provided a combination treatment comprising the administration of an effective amount of a compound of the formula (I), or a pharmaceutically acceptable salt, solvate, solvate of such a salt or a prodrug thereof, optionally together with a pharmaceutically acceptable diluent or carrier, with the simultaneous, sequential or separate administration of an effective amount of a PPAR alpha and/or gamma agonist, or a pharmaceutically acceptable salt, solvate, solvate of such a salt or a prodrug thereof, optionally together with a pharmaceutically acceptable diluent or carrier to a warm-blooded animal, such as man in need of such therapeutic treatment.

In addition to their use in therapeutic medicine, the compounds of formula (I), or a pharmaceutically acceptable salt, solvate, solvate of such a salt or a prodrug thereof, are also useful as pharmacological tools in the development and standardisation of in vitro and in vivo test systems for the evaluation of the effects of inhibitors of IBAT in laboratory animals such as cats, dogs, rabbits, monkeys, rats and mice, as part of the search for new therapeutic agents.

Many of the intermediates described herein are novel and are thus provided as a further feature of the invention. For example compounds of formula (IVa), (IVb), (VIa), (VIb), (VIIIa) and (VIIIb) show IBAT inhibitory activity when tested in the above referenced in vitro test assay.

Thus in a further feature of the invention, there is provided a compound of formula (IVa), (IVb), (VIa), (VIb), (VIIIa) or (VIIIb), or a pharmaceutically acceptable salt, solvate, solvate of such a salt or a prodrug thereof; with the proviso that when $R^{11}$ and $R^{12}$ are selected from carbocyclyl and/or heterocyclyl, said carbocyclyl and heterocyclyl are not totally unsaturated.

Therefore according to a further aspect of the invention there is provided a pharmaceutical composition which comprises a compound of formula (IVa), (IVb), (VIa), (VIb), (VIIIa) or (VIIIb), or a pharmaceutically acceptable salt, solvate, solvate of such a salt or a prodrug thereof, as defined hereinbefore in association with a pharmaceutically-acceptable diluent or carrier; with the proviso that when $R^{11}$ and $R^{12}$ are selected from carbocyclyl and/or heterocyclyl, said carbocyclyl and heterocyclyl are not totally unsaturated.

According to an additional aspect of the present invention there is provided a compound of the formula (IVa), (IVb), (VIa), (VIb), (VIIIa) or (VIIIb), or a pharmaceutically acceptable salt, solvate, solvate of such a salt or a prodrug thereof, as defined hereinbefore for use in a method of prophylactic or therapeutic treatment of a warm-blooded animal, such as man; with the proviso that when $R^{11}$ and $R^{12}$ are selected from carbocyclyl and/or heterocyclyl, said carbocyclyl and heterocyclyl are not totally unsaturated.

Thus according to this aspect of the invention there is provided a compound of the formula (IVa), (IVb), (VIa), (VIb), (VIIIa) or (VIIIb), or a pharmaceutically acceptable salt, solvate, solvate of such a salt or a prodrug thereof, as defined hereinbefore for use as a medicament; with the proviso that when $R^{11}$ land $R^{12}$ are selected from carbocyclyl and/or heterocyclyl, said carbocyclyl and heterocyclyl are not totally unsaturated.

According to another feature of the invention there is provided the use of a compound of the formula (IVa), (IVb), (VIa), (VIb), (VIIIa) or (VIIIb), or a pharmaceutically acceptable salt, solvate, solvate of such a salt or a prodrug thereof as defined hereinbefore in the manufacture of a medicament for use in the production of an IBAT inhibitory effect in a warm-blooded animal, such as man; with the proviso that when $R^{11}$ and $R^{12}$ are selected from carbocyclyl and/or heterocyclyl, said carbocyclyl and heterocyclyl are not totally unsaturated.

According to another feature of the invention there is provided the use of a compound of the formula (IVa), (IVb), (VIa), (VIb), (VIIIa) or (VIIIb), or a pharmaceutically acceptable salt, solvate, solvate of such a salt or a prodrug thereof as defined hereinbefore in the manufacture of a medicament for use in the treatment of hyperlipidaemic conditions in a warm-blooded animal, such as man; with the proviso that when $R^{11}$ and $R^{12}$ are selected from carbocyclyl and/or heterocyclyl, said carbocyclyl and heterocyclyl are not totally unsaturated.

According to a further feature of this aspect of the invention there is provided a method for producing an IBAT inhibitory effect in a warm-blooded animal, such as man, in need of such treatment which comprises administering to said animal an effective amount of a compound of formula (IVa), (IVb), (VIa), (VIb), (VIIIa) or (VIIIb), or a pharmaceutically acceptable salt, solvate, solvate of such a salt or a prodrug thereof; with the proviso that when $R^{11}$ and $R^{12}$ are selected from carbocyclyl and/or heterocyclyl, said carbocyclyl and heterocyclyl are not totally unsaturated.

According to a further feature of this aspect of the invention there is provided a method of treating hyperlipidemic conditions in a warm-blooded animal, such as man, in need of such treatment which comprises administering to said animal an effective amount of a compound of formula (IVa), (IVb), (VIa), (VIb), (VIIIa) or (VIIIb), or a pharmaceutically acceptable salt, solvate, solvate of such a salt or a prodrug thereof; with the proviso that when $R^{11}$ and $R^{12}$ are selected from carbocyclyl and/or heterocyclyl, said carbocyclyl and heterocyclyl are not totally unsaturated.

In the above other pharmaceutical composition, process, method, use and medicament manufacture features, the alternative and preferred embodiments of the compounds of the invention described herein also apply.

EXAMPLES

The invention will now be illustrated in the following non limiting examples, in which standard techniques known to the skilled chemist and techniques analogous to those described in these examples may be used where appropriate, and in which, unless otherwise stated:

(i) evaporations were carried out by rotary evaporation in vacuo and work up procedures were carried out after removal of residual solids such as drying agents by filtration;

(ii) all reactions were carried out under an inert atmosphere at ambient temperature, typically in the range 18-25° C., with solvents of HPLC grade under anhydrous conditions, unless otherwise stated;

(iii) column chromatography (by the flash procedure) was performed on Silica gel 40-63 μm (Merck);

(iv) yields are given for illustration only and are not necessarily the maximum attainable;

(v) the structures of the end products of the formula (I) were generally confirmed by nuclear (generally proton) magnetic resonance (NMR) and mass spectral techniques; magnetic resonance chemical shift values were measured in deuterated $CD_3OD$ (unless otherwise stated) on the delta scale (ppm downfield from tetramethylsilane); proton data is quoted unless otherwise stated; spectra were recorded on a Varian Mercury-300 MHz, Varian Unity plus-400 MHz, Varian Unity plus-600 MHz or on Varian Inova-500 MHz spectrometer; and peak multiplicities are shown as follows: s, singlet; d, doublet; dd, double doublet; t, triplet; tt, triple triplet; q, quartet; tq, triple quartet; m, multiplet; br, broad; LCMS were recorded on a Waters ZMD, LC column xTerra MS $C_8$ (Waters), detection with a HP 1100 MS-detector diode array equipped; mass spectra (MS) (loop) were recorded on VG Platform II (Fisons Instruments) with a HP-1100 MS-detector diode array equipped; unless otherwise stated the mass ion quoted is $(MH^+)$, (vi) unless further details are specified in the text, analytical high performance liquid chromatography (HPLC) was performed on Prep LC 2000 (Waters), Kromasil $C_8$, 7 μm, (Akzo Nobel); MeCN and de-ionised water 100 mM ammonium acetate as mobile phases, with suitable composition;

(vii) intermediates were not generally fully characterised and purity was assessed by thin layer chromatography (TLC), HPLC, infra-red (IR), MS or NMR analysis;

(viii) where solutions were dried sodium sulphate was the drying agent;

(ix) where an "ISOLUTE" column is referred to, this means a column containing 2 g of silica, the silica being contained in a 6ml disposable syringe and supported by a porous disc of 54 Å pore size, obtained from International Sorbent Technology under the name "ISOLUTE"; "ISOLUTE" is a registered trade mark;

(x) the following abbreviations may be used hereinbefore or hereinafter:—
DCM dichloromethane;
DMF N,N-dimethylformamide;
TFA trifluoroacetic acid;
TBTU o-Benzotriazol-1-yl-N,N,N',N'-tetramethyluronium tetrafluoroborate;
EtOAc ethyl acetate; and
MeCN acetonitrile.

Example 1

(±)-trans-1,1-Dioxo-3-ethyl-3-butyl-5-phenyl-8 (N-{(R)-α-[N'-(2-(S)-3-(R)-4-(R 5-(R)-2,3,4,5,6-pentahydroxyhexyl)carbamoyl]benzyl}carbamoylmethoxy)-2,3,4,5-tetrahydro-1,4-benzothiazepine (±)-trans-1,1-Dioxo-3-ethyl-3-butyl-5-phenyl-8-(carboxymethoxy)-2,3,4,5-tetrahydro-1,4-benzothiazepine (Method 2; 20 mg, 0.043 mmol), (R)-α-[N'-(2-(S)-3-(R)-4-(R)-5-(R)-2,3,4,5,6-pentahydroxyhexyl)carbamoyl]benzylamine (Method 10; 19 mg, 0.064 mmol) and N-methylmorpholine (27 mg, 0.26 mg) were dissolved in DMF and stirred at room temperature. TBTU (19 mg, 0.059) mmol was added and the reaction mixture was stirred for 2 hours. LC-MS indicated no unreacted starting material. A small amount of water and acetonitrile was added and the product was purified by preparative HPLC on a C8 column using a gradient from 5% to 100% MeCN in 0.1M ammonium acetate buffer as mobile phase. Lyophilisation gave 27 mg of the title compound. NMR (400 MHz, $CD_3OD$): 0.81 (t, 3H), 0.89 (t, 3H), 1.11-1.35 (m, 4H), 1.4-1.5 (m, 1H), 1.52-1.63 (m, 1H), 1.74-1.85 (m, 1H), 1.94 (s, 3H), 2.27-2.28 (m, 1H), 3.11-3.25 (m, 2H), 3.46-3.53 (m, 2H), 3.53-3.75 (m, 5H), 3.78-3.84 (m, 1H), 4.63-4.66 (m, 1H), 5.51 (s, 1H), 6.0 (s, 1H), 6.59-6.64 (m, 1H), 6.95-7.01 (m, 1H), 7.27-7.35 (m, 4H), 7.35-7.41 (m, 6H), 7.66 (t, 1H).

Example 2

(±)-trans-1,1-Dioxo-3-ethyl-3-butyl-5-phenyl-7-methylthio-8-(N-{(R)-α-[N'-(2-(S)-3-(R)-4-(R)-5-(R)-2,3,4,5,6-pentahydroxyhexyl)carbamoyl]benzyl}carbamoylmethoxy)-2,3,4,5-tetrahydro-1,4-benzothiazepine 3,5-trans-1,1-Dioxo-3-ethyl-3-butyl-5-phenyl-7-methylthio-8-(N—{(R)-α-[N-(carboxymethyl)carbamoyl]benzyl}carbamoylmethoxy)-2,3,4,5-tetrahydro-1,4-benzothiazepine (Method 6; 2 mg, 3 μmol) was dissolved in 0.5 ml DMF. (D)-Glucamine (2 mg, 11 μmol), N-methyl morpholine (ca 1 μl, 91 μmol) and TBTU (1.1 mg, 4 μmol) were added and the solution was stirred for 3 hours. The reaction was completed according to LC/MS-analysis. The product was purified by preparative HPLC on a C8 column using a gradient from 5% to 100% MeCN in 0.1M ammonium acetate buffer as mobile phase. The product fraction was lyophilised to yield 2.4 mg (95%). LC/Micromass Q TOF micro MS analysis showed four peaks corresponding to four isomers of the product with a total purity of 96%; m/z=831.328.

Example 3

1,1-Dioxo-3-ethyl-3-butyl-4-hydroxy-5-phenyl-7-(N-{α-[N'-(2-(S)-3-(R)-4-(R)-5-(R)-2,3,4,5,6-pentahydroxyhexyl)carbamoyl]-2-fluorobenzyl}carbamoylmethylthio)-2,3,4,5-tetrahydrobenzothiepine 1,1-Dioxo-3-butyl-3-ethyl-4-hydroxy-5-phenyl-7-{N-[α-(carboxy)-2-fluorobenzyl]carbamoylmethylthio}-2,3,4,5-tetrahydrobenzothiepine (Method 3; 28 mg, 0.046 mmol) and D-glucamine (10 mg, 0.055 mmol) were added to DMF (2.0 ml) and 2,6-lutidine (0.02 ml, 0.14 mmol) was added. When everything had dissolved TBTU (20 mg, 0.060 mmol) was added and the reaction mixture was stirred at ambient temperature overnight. More D-glucamine (10 mg, 0.055 mmol) and TBTU (20 mg, 0.060 mmol) were added and the reaction mixture was stirred for another 3 hours. The reaction mixture was purified by preparative HPLC using MeCN/ammonium acetate buffer (gradient 50:50 to 100:0) to give the title compound (9.0 mg, 25%). NMR (400 MHz, DMSO-d6): 0.73 (t, 3H), 0.83 (t, 3H), 1.00 (m, 1H), 1.20-1.45 (m, 5H), 1.59 (m, 1H), 2.01 (m, 1H), 3.10 (m, 2H), 3.94 (s, 1H), 5.22 (d, 1 H), 5.60 (d, 1H), 6.41 (dd, 1H), 7.13 (m, 3H), 7.25-7.43 (m, 8H), 7.74 (dd, 1H), 8.08 (br s, 1H), 8.89 (br s, 1H).

Example 4

1,1-Dioxo-3-butyl-3-ethyl-4-hydroxy-5-phenyl-7-(N-{1-[N'-(2-(S)-3-(R)-4-(R)-5-(R)-2,3,4,5,6-pentahydroxyhexyl)carbamoyl]-1-(cyclohexyl)methyl}carbamoylmethylthio)-2,3,4,5-tetrahydrobenzothiepine 1,1-Dioxo-3-butyl-3-ethyl-4-hydroxy-5-phenyl-7-{N-[1-(carboxy)-1-(cyclohexyl)methyl]carbamoylmethylthio}-2, 3,4,5-tetrahydrobenzothiepine (Method 5; 4 mg, 0.0066 mmol), D-glucamine (2 mg, 0.0088 mmol) and N-methyl-morpholine (4 mg, 0.035 mmol) were dissolved in DMF and stirred at room temperature for 10 min. TBTU (0.003 mg, 0.0087 mmol) and the reaction mixture was stirred over night. A small amount of water and acetonitrile was added and the product was purified by preparative HPLC on a C8 column using a gradient from 5% to 100% MeCN in 0.1% M ammonium acetate buffer as mobile phase. Lyophilization gave (1.7 mg 33.4%) of the title compound. LC/MicromassQ TOF micro MS analysis showed two peaks corresponding to two isomers of the product with a total purity of 96%; m/z=765.343

Preparation of Starting Materials

The starting materials for the Examples above are either commercially available or are readily prepared by standard Methods from known materials. For example, the following reactions are an illustration, but not a limitation, of some of the starting materials used in the above reactions.

Method 1

(±)-trans-1,1-Dioxo-3-ethyl-3-butyl-5-phenyl-8-(t-butoxycarbonylmethoxy)-2,3,4,5-tetrahydro-1,4-benzothiazepine A mixture of (±)-trans-1,1-dioxo-3-butyl-3-ethyl-5-phenyl-8-hydroxy-2,3,4,5-tetrahydro-1,4-benzothiazepine (prepared according to WO/9605188; 52 mg, 0.14 mmol), t-butyl bromoacetate (32 mg, 0.16 mmol), potassium carbonate (76 mg, 0.55 mmol) and cesium carbonate (12 mg, 0.036 mmol) in acetonitrile was stirred at 50 C for 2 hours. The solvent was removed at reduced pressure and the crude product was purified by chromatography. The eluent was initially DCM and thereafter switched to EtOAc:DCM, 1:10. 0.055 g of the desired product was obtained.

Method 2

(±)-trans-1,1-Dioxo-3-ethyl-3-butyl-5-phenyl-8-(carboxymethoxy)-2,3,4,5-tetrahydro-1,4-benzothiazepine (±)-trans-1,1-Dioxo-3-ethyl-3-butyl-5-phenyl-8-(t-butoxycarbonylmethoxy)-2,3,4,5-tetrahydro-1,4-benzothiazepine (Method 1; 58 mg, 0.12 mmol) was dissolved in formic acid and stirred for 20 hours at ambient temperature and then for 4 hours at 45° C. The formic acid was removed at reduced pressure. Toluene was added to the residue and the toluene and remaining formic acid were removed at reduced pressure to give the desired product (50 mg, 0.12 mmol).

Method 3

1,1-Dioxo-3-butyl-3-ethyl-4-hydroxy-5-phenyl-7-{N-[α-(carboxy)-2-fluorobenzyl]carbamoylmethylthio}-2,3,4,5-tetrahydrobenzothiepine 1,1-Dioxo-3-butyl-3-ethyl-4-hydroxy-5-phenyl-7-(carboxymethylthio)-2,3,4,5-tetrahydrobenzothiepine (Method 4; 59 mg, 0.13 mmol) and methyl amino(2-fluorophenyl) acetate hydrochloride (40 mg, 0.18 mmol) were added to DCM (3.0 ml) and 2,6-lutidine (0.04 ml, 0.38 mmol) was added. The reaction mixture was stirred at ambient temperature for 5 min and TBTU (58 mg, 0.18 mmol) was added. After stirring at ambient temperature for 3 hours the reaction mixture was diluted with DCM (5 ml) and was washed with HCl (aq., 1 M, 5 ml). The solvent was evaporated and the residue was dissolved in THF (2.0 ml) and water (1.0 ml) and NaOH (aq., 1 M, 0.30 mmol) was added. After stirring at ambient temperature for 2 h the reaction mixture was quenched with HCl (aq., 1 M), diluted with water (10 ml) and extracted with DCM (3×5 ml). The combined organic layers were purified with preparative HPLC MeCN/ammonium acetate buffer 40:60 to give the title compound (70 mg, 89%). NMR (400 MD, DMSO-$d_6$): 0.74 (t, 3H), 0.84 (t, 3H), 1.00 (m, 1 H), 1.18-1.46 (m, 5H), 1.60 (m, 1H), 2.02 (m, 1H), 3.11 (m, 2H), 3.69 (m, 2H), 3.94 (s, 1 H), 5.04 (t, 1H), 5.23 (d, 1H), 6.44 (d, 1H), 6.94-7.44 (m, 11H), 7.70 (t, 1H), 8.40 (m, 1H).

Method 4

1,1-Dioxo-3-butyl-3-ethyl-4-hydroxy-5-phenyl-7-(carboxymethylthio)-2,3,4,5-tetrahydrobenzothiepine 1,1-Dioxo-3-butyl-3-ethyl-4-hydroxy-5-phenyl-7-fluoro-2,3,4,5-tetrahydrobenzothiepine (prepared according to WO 98/40375; 300 mg, 0.77 mmol) was dissolved in DMF (3 ml) and caesium carbonate (540 mg, 1.66 mmol) was added followed by ethyl thioglycolate (0.17 ml, 1.54 mmol) and the reaction mixture was subjected to microwave irradiation in a Smith Synthesiser at 100° C. for 5 min. The reaction mixture was added to water (25 ml), extracted with DCM (5×5 ml) and concentrated. The crude ethyl ester was dissolved in THF (4 ml) and water (2 ml) and NaOH (1 M, 4 ml) was added. The reaction mixture was stirred at ambient temperature for 6 hours, quenched with HCl (1 M), diluted with water (25 ml) and extracted with DCM (4×5 ml). The combined organic layers were purified with preparative HPLC using MeCN/ ammonium acetate buffer as the eluent (50:50) to give the title compound (172 mg, 48%). NMR (400 MHz, DMSO-$d_6$): 0.74 (t, 3H), 0.84 (t, 3H), 1.01 (m, 1), 1.18-1.46 (m, 5H), 1.60 (m, 1H), 2.02 (m, 1H), 3.07/3.12 (ABq, 2H), 3.33/3.39 (ABq, 2H), 3.95 (s, 1H), 5.23 (s, 1H), 6.38 (d, 1H), 7.19 (dd, 1H), 7.34 (m, 1H), 7.42 (m, 4H), 7.73 (d, 1H).

Method 5

1,1-Dioxo-3-butyl-3-ethyl-4-hydroxy-5-phenyl-7-{N-[1-(carboxy)-1-(cyclohexyl)methyl]carbamoylmethylthio}-2,3,4,5-tetrahydrobenzothiepine The title compound was synthesised according to the same procedure as Method 3 but using methyl amino(cyclohexyl) acetate hydrochloride as starting material. NMR (400 MHz, DMSO-d6): 0.74 (t, 3H), 0.84 (t, 3H), 0.92-1.10 (m, 6H), 1.20-1.66 (m, 12 H), 2.01 (m, 1 H), 3.07/3.13 (ABq, 2H), 3.60-3.75 (m, 3H), 3.95 (m, 2H), 5.24 (s, 1H), 6.44 (m, 1H), 7.33 (m, 1H), 7.41 (m, 4H), 7.75 (d, 1H), 7.98 (t, 1H).

Method 6

3,5-trans-1,1-Dioxo-3-ethyl-3-butyl-5-phenyl-7-methylthio-8-(N—{(R)-α-[N-(carboxymethyl)carbamoyl]benzyl}carbamoylmethoxy)-2,3,4,5-tetrahydro-1,4-benzothiazepine 3,5-trans-1,1-Dioxo-3-ethyl-3-butyl-5-phenyl-7-methylthio-8-(carboxymethoxy)-2,3,4,5-tetrahydro-1,4-benzothiazepine (Method 7; 50 mg, 0.105 mmol) was dissolved in DCM (2 ml). 2,6-Lutidine (0.025 ml, 0.215 mmol), TBTU (45 mg, 0.140 mmol) and (R)-α-[N-(t-butoxycarbonylmethyl)carbamoyl]benzylamine (3 mg, 0.163 mmol) were added successively. The mixture was stirred for 2 hours at ambient temperature. The solution was concentrated and the intermediate ester was purified by chromatography on silica using DCM/EtOAc (9/1) as eluent. The solvent was evaporated to yield 45 mg (60%). M/z: 724. The ester was dissolved in 3 ml DCM and hydrolysed by addition of TFA (1 ml). After 2 hours the mixture was concentrated and purified using preparative HPLC. A gradient of MeCN from 40% to 60% in 0.1 M ammonium acetate buffer was used as eluent. Lyophilisation yielded 33 mg (80%). NMR (400 MHz): 0.75-0.85 (m, 3H), 0.85-0.95 (m, 3H), 1.1-1.65 (m, 6H), 1.75-1.9 (m, 1H), 2.0 (s, 3H), 2.2-2.4 (m, 1H), 3.1-3.55 (m, 2H), 3.85 (ABq, 2H), 4.6-4.8 (m, 2H), 5.6 (s, 1H), 5.98-6.03 (m, 1H), 6.4 (s, 1H), 7.25-7.56 (m, 11H); m/z: 668.

Method 7

3,5-trans-1,1-Dioxo-3-ethyl-3-butyl-5-phenyl-7-methylthio-8-(carboxymethox-y)-2,3,4,5-tetrahydro-1,4-benzothiazepine The title compound was prepared from 3,5-trans-1,1-dioxo-3-ethyl-3-butyl-5-phenyl-7-methylthio-8-hydroxy-2,3,4,5-tetrahydro-1,4-benzothiazepine (Method 8; 153 mg, 0.36 mmol), ethylbromoacetate (75 mg, 0.45 mmol), sodium carbonate (162 mg, 1.52 mmol) and tetrabutylammonium bromide (12 mg, 0.037 mmol) in acetonitrile (10 ml). The intermediate ethyl ester was extracted between diluted HCl and DCM. The DCM phase was washed with brine, dried with Na$_2$SO$_4$ and concentrated. M/z 506. The crude product was dissolved in THF/H$_2$O (3/1; 4 ml) and LiOH (22 mg, 0.91 mmol) was added. The mixture was stirred for 2 h and the solvent was removed under reduced pressure. The crude product was purified using preparative HPLC. A gradient from 40% to 60% MeCN in 0.1 M ammonium acetate buffer was used as eluent. The MeCN was removed under reduced pressure and the remaining aqueous solution was acidified using 5% HCl and was then extracted with DCM. The DCM layer was dried with Na$_2$SO$_4$ and concentrated. The crude product was co-evaporated with diethyl ether. The obtained crystals were filtered off and dried. Mass: 158 mg (91%). NMR 0.75 (t, 3H), 0.9 (t, 3H), 1.1-1.7 (m, 6H), 1.7-1.9 (m, 1H), 2.0 (s, 3H), 2.2-2.4 (m, 1H), 3.3 (dd, 2H), 4.75 (s, 2H), 6.0 (s, 1H), 6.4 (s, 1H), 7.3-7.5 (m, 6H); m/z: 478.

Method 8

3,5-trans-1,1-Dioxo-3-ethyl-3-butyl-5-phenyl-7-methylthio-8-hydroxy-2,3,4,5-tetrahydro-1,4-benzothiazepine (±)-trans-7-Bromo-3-butyl-3-ethyl-2,3,4,5-tetrahydro-8-methoxy-5-phenyl-1,4-benzothiazepine 1,1-dioxide (prepared according to WO 96/05188; 300 mg, 0.64 mmol) was dissolved in 5 ml DMF under N$_2$(g)-atmosphere. Sodium thiomethylate (150 mg, 2.14 mmol) was added and the mixture was heated to 110° C. for 2 h. The solvent was removed under reduced pressure and the residue was extracted between 5% HCl and EtOAc. The organic phase was washed with brine, dried with Na$_2$SO$_4$ and concentrated. The product was purified using preparative HPLC. A gradient from 40% to 100% of MeCN in 0.1 M ammonium acetate buffer was used as eluent. Lyophilisation yielded 153 mg, 57%. M/z: 420.

Method 9

(N—{(R)-α-[N'-(2-(S)-3-(R)-4-(R)-5-(R)-2,3,4,5,6-Pentahydroxyhexyl)carbamoyl]benzyl}carbamoyl)oxymethylphenyl (2R)-{[(Benzyloxy)carbonyl]amino}(phenyl)acetic acid (2.07 g, 7.26 mmol), (2R,3R,4R,5S)-6-aminohexane-1,2,3,4,5-pentol (1.44 g, 7.9 mmol) and 2,6-dimethylpyridine (0.933 g, 8.7 mmol) were dissolved in DMF (30 ml). TBTU (3.80 g, 8.7 mmol) was added and the mixture was stirred for 1.5 hour. (2R,3R,4R,5S)-6-aminohexane-1,2,3,4,5-pentol (0.21 g, 0.2 mmol) was added and the mixture was stirred for 1 hour. The solvent was evaporated under reduced pressure. The mixture was dissolved in isopropanol (35 ml), heated to 80-100° C. The mixture was then allowed to reach room temperature. The formed crystals was filtered off and washed with isopropanol (2×20 ml) and two times with diethyl ether (2×25 ml). The crystals was recrystallized using isopropanol (100 ml) heated to reflux. The mixture was then allowed to reach room temperature. The crystals was filtered off and washed with small portions of isopropanol (totally 170 ml) and with diethyl ether (2×50 ml) to yield 2.517 g (77%) of the product. NMR (600 M, CD$_3$OD): 3.15-3.23 (m, 1H), 3.48 (dd, 1H), 3.53-3.68 (m, 4H), 3.71 (dd, 1H), 3.77-3.83 (m, 1H), 5.08 (s, 2H), 5.20 (s, 1H), 7.24-7.36 (m, 8H), 7.39 (brd, 2H).

Method 10

(R)-α-[N'-(2-(S)-3-(R)-4-(R)-5-(R)-2,3,4,5,6-Pentahydroxyhexyl)carbamoyl]benzylamine (N—{(R)-α-[N'-(2-(S)-3-(R)-5-(R)-2,3,4,5,6-Pentahydroxyhexyl)carbamoyl]benzyl}carbamoyl)oxymethylphenyl (Method 9; 2.46 g, 5.49 mmol), palladium on activated carbon (5%, 0.535 g) and water (1.5 ml) were dissolved in ethanol (80 ml). The mixture was treated under H2-atmosphere overnight. The mixture was filtered through hyflo and the solvent was evaporated under reduced pressure to yield 1.543 g (89.5%) of the title compound. NMR (400 MHz, CD$_3$OD): 3.23 (dd, 1H), 3.49 (dd, 1H), 3.56-3.62 (m, 2H), 3.63-3.70 (m, 2H), 3.73 (dd, 1H), 3.79-3.84 (m, 1H), 4.48 (s, 1H), 7.25-7.37 (m, 3H), 7.41 (brd, 2H).

The invention claimed is:
1. A compound of formula (I):

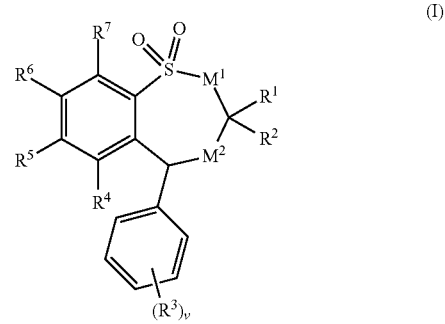

wherein
M$^1$ is —CH$_2$—;
M$^2$ is —NR$^{24}$—;
one of R$^1$ and R$^2$ is selected from hydrogen or C$_{1-6}$alkyl and the other is selected from C$_{1-6}$alkyl;
v is 0;
R$^4$ and R$^7$ are hydrogen;
one of R$^5$ and R$^6$ is a group of formula (IA):

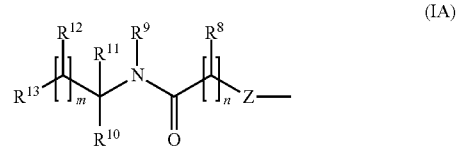

and the other of R$^5$ and R$^6$ is hydrogen or methylthio;
Z is —O—;
R$^8$ is hydrogen;
R$^9$ is hydrogen;
R$^{10}$ is selected from cyclohexyl, and phenyl optionally substituted by one or more substituents R$^{28}$;
R$^{11}$ is hydrogen;

$R^{13}$ is a group of formula (IB):

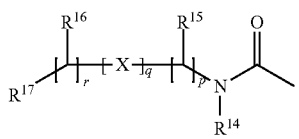

wherein:
$R^{14}$ is hydrogen;
$R^{15}$ is hydrogen;
$R^{16}$ is hydroxy;
$R^{17}$ is ethyl substituted on each carbon by one $R^{47}$, wherein $R^{47}$ is hydroxyl, or $R^{17}$ is a group of formula (IC);

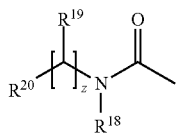

wherein:
$R^{18}$ is hydrogen;
$R^{19}$ is hydrogen;
$R^{20}$ is $C_{1-10}$alkyl; wherein $R^{20}$ may be independently optionally substituted on carbon by one or more $R^{57}$; wherein $R^{57}$ is selected from halo or hydroxyl;
p is 1;
q is 0;
r is 3;
m is 0;
n is 1;
z is 0-3;
$R^{24}$ is hydrogen; and
each $R^{28}$ is selected from halo, hydroxy, and $C_{1-10}$alkoxy;
or a pharmaceutically acceptable salt or an in vivo hydrolysable ester thereof, wherein the hydrolysable ester is selected from the group consisting of: α-acyloxyalkyl ethers selected from acetoxymethoxy and 2,2-dimethylpropionyloxy-methoxy; and in vivo hydrolysable ester forming groups for hydroxy selected from alkanoyl, benzoyl, phenylacetyl, alkoxycarbonyl, dialkylcarbamoyl, N-(dialkylaminoethyl)-N-alkylcarbamoyl, dialkylaminoacetyl, and carboxyacetyl.

2. A compound according to claim 1 wherein one of $R^1$ and $R^2$ is $C_{1-4}$-alkyl.

3. A compound having formula: (+/−)-trans-1,1-dioxo-3-ethyl-3-butyl-5-phenyl-7-methylthio-8-(N-{(R)-α-[N'-(2-(S)-3-(R)-4-(R)-5-(R)-2,3,4,5,6-pentahydroxyhexyl)carbamoyl]benzyl}carbamoylmethoxy)-2,3,4,5-tetrahydro-1,4-benzothiazepine, or a pharmaceutically acceptable salt or an in vivo hydrolysable ester thereof, wherein the hydrolysable ester is selected from the group consisting of: α-acyloxyalkyl ethers selected from acetoxymethoxy and 2,2-dimethylpropionyloxy-methoxy; and in vivo hydrolysable ester forming groups for hydroxy selected from alkanoyl, benzoyl, phenylacetyl, alkoxycarbonyl, dialkylcarbamoyl, N-(dialkylaminoethyl)-N-alkylcarbamoyl, dialkylaminoacetyl, and carboxyacetyl.

4. A process for preparing a compound of formula (I) or a pharmaceutically acceptable salt or an in vivo hydrolysable ester thereof, as claimed in claim 1, which process comprises of:

Process 1): for compounds of formula (I); reacting a compound of formula (IIa):

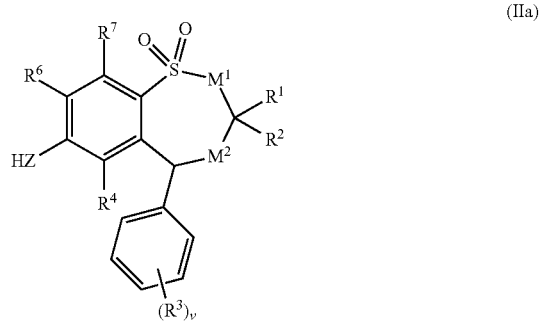

with a compound of formula (III):

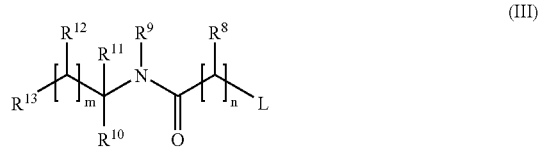

wherein L is a displaceable group;
Process 2): reacting an acid of formula (IVa):

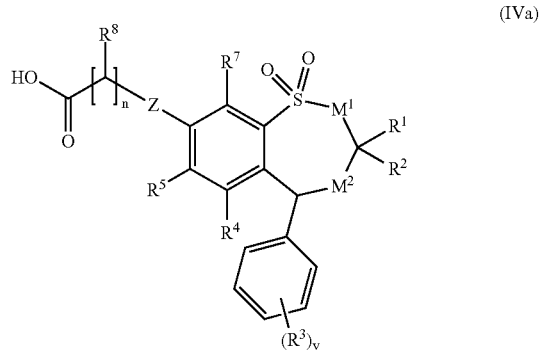

with an amine of formula (V):

Process 3): for compounds of formula (I) wherein $R^{13}$ is a group of formula (IB); reacting an acid of formula (VIa):

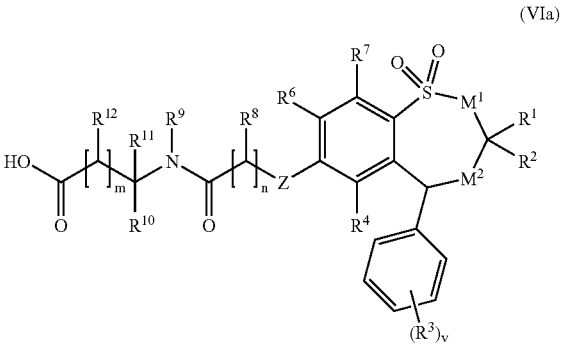

with an amine of formula (VI):

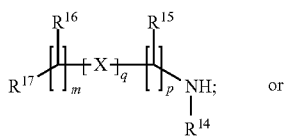
(VI)

Process 4) for compounds of formula (I) wherein $R^6$ is methylthio ; reacting a compound of formula (Xb):

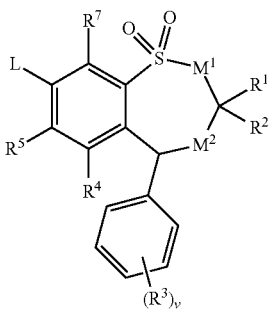
(Xb)

wherein L is a displaceable group; with a thiol of formula (XI):

$$R^m\text{—H} \qquad (XI)$$

wherein $R^m$ is methylthio;

and optionally:
i) converting a compound of the formula (I) into another compound of the formula (I);
ii) removing any protecting groups;
iii) forming a pharmaceutically acceptable salt or a prodrug.

5. A pharmaceutical composition which comprises a compound of formula (I), or a pharmaceutically acceptable salt or an in vivo hydrolysable ester thereof, as in claim 1, in association with a pharmaceutically-acceptable diluent or carrier, wherein the hydrolysable ester is selected from the group consisting of: α-acyloxyalkyl ethers selected from acetoxymethoxy and 2,2-dimethylpropionyloxy-methoxy; and in vivo hydrolysable ester forming groups for hydroxy selected from alkanoyl, benzoyl, phenylacetyl, alkoxycarbonyl, dialkylcarbamoyl, N-(dialkylaminoethyl)-N-alkylcarbamoyl, dialkylaminoacetyl, and carboxyacetyl.

* * * * *

UNITED STATES PATENT AND TRADEMARK OFFICE
CERTIFICATE OF CORRECTION

PATENT NO. : 8,067,584 B2
APPLICATION NO. : 10/546005
DATED : November 29, 2011
INVENTOR(S) : Ingemar Starke It is certified that error appears in the above-identified patent and that said Letters Patent is hereby corrected as shown below:

First Page, Primary Examiner, Line 1, please delete "O Dell" and insert -- O'Dell --, therefor;

Column 45, Line 50 (Claim 2), please delete "$C_{1-4}$-alkyl." and insert -- $C_{1-4}$alkyl. --, therefor;

Column 46, Lines 27-40 (Claim 4), please delete " 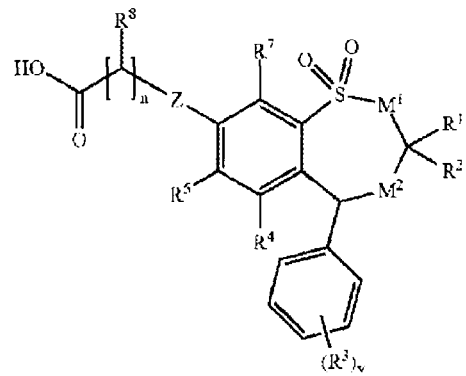 "

and insert -- 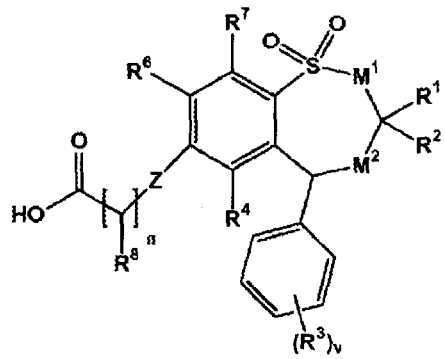 --, therefor;

Signed and Sealed this
Twenty-first Day of February, 2012

David J. Kappos
*Director of the United States Patent and Trademark Office*

CERTIFICATE OF CORRECTION (continued)
U.S. Pat. No. 8,067,584 B2

Column 47, Lines 3-8 (Claim 4), please delete " 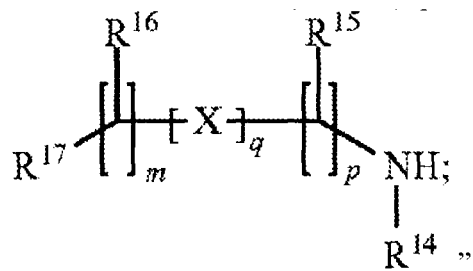

and insert -- 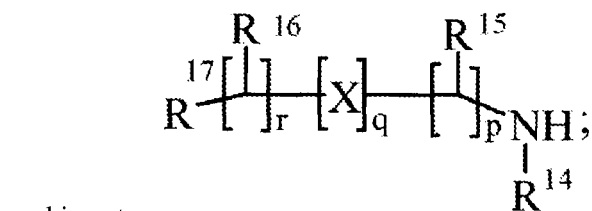 --, therefor;

Column 47, Line 10 (Claim 4), please delete "methylthio ;" and insert -- methylthio; --, therefor;

Column 48, Lines 10-11 (Claim 4), please delete "a prodrug." and insert -- an in vivo hydrolysable ester thereof. --, therefor.